US009272015B2

(12) United States Patent
Kim et al.

(10) Patent No.: US 9,272,015 B2
(45) Date of Patent: *Mar. 1, 2016

(54) METHOD FOR ACHIEVING DESIRED GLIAL GROWTH FACTOR 2 PLASMA LEVELS

(71) Applicant: Acorda Therapeutics, Inc., Ardsley, NY (US)

(72) Inventors: Haesun Kim, Teaneck, NJ (US); Anthony O. Caggiano, Larchmont, NY (US)

(73) Assignee: Acorda Therapeutics, Inc., Ardsley, NY (US)

( * ) Notice: Subject to any disclaimer, the term of this patent is extended or adjusted under 35 U.S.C. 154(b) by 102 days.

This patent is subject to a terminal disclaimer.

(21) Appl. No.: 13/853,386

(22) Filed: Mar. 29, 2013

(65) Prior Publication Data

US 2013/0345131 A1 Dec. 26, 2013

Related U.S. Application Data

(63) Continuation of application No. 12/380,760, filed on Mar. 2, 2009, now Pat. No. 8,410,050.

(60) Provisional application No. 61/067,589, filed on Feb. 29, 2008.

(51) Int. Cl.
*A61K 38/18* (2006.01)

(52) U.S. Cl.
CPC .............. *A61K 38/18* (2013.01); *A61K 38/1883* (2013.01)

(58) Field of Classification Search
None
See application file for complete search history.

(56) References Cited

U.S. PATENT DOCUMENTS

| | | | |
|---|---|---|---|
| 5,530,109 | A | 6/1996 | Goodearl et al. |
| 5,716,930 | A | 2/1998 | Goodearl et al. |
| 6,972,280 | B2 | 12/2005 | Goodearl et al. |
| 7,037,888 | B1 | 5/2006 | Sklar et al. |
| 7,135,456 | B1 | 11/2006 | Goodearl et al. |
| 7,319,019 | B1 | 1/2008 | Goodearl et al. |
| 7,776,817 | B2 | 8/2010 | Ford |
| 7,973,007 | B2 | 7/2011 | Ford |
| 2008/0213817 | A1* | 9/2008 | Karin et al. ............... 435/29 |

FOREIGN PATENT DOCUMENTS

| | | | |
|---|---|---|---|
| WO | WO-9404560 A1 | 3/1994 |
| WO | WO-9709425 A1 | 3/1997 |
| WO | WO 0135899 A2 | 5/2001 |
| WO | WO 03082898 A2 | 10/2003 |
| WO | WO-2004110359 A3 | 8/2006 |
| WO | WO-2006084116 A2 | 8/2006 |
| WO | WO-2012021818 A2 | 2/2012 |

OTHER PUBLICATIONS

Parkinson et al. "Krox-20 Inhibits Jun-NH$_2$-Terminal Kinase/c-Jun to Control Schwann Cell Proliferation and Death." *J. Cell. Biol.* 164.3(2004):385-394.
"Consensus Recommendations for the Management of Chronic Heart Failure." *Am. J. Cardiol.* 83.2A(1999):1A-38A.
Berge et al. "Pharmaceutical Salts." *J. Pharm. Sci.* 66.1(1977):1-19.
Bian et al. "Neuregulin-1 Attenuated Doxorubicin-Induced Decrease in Cardiac Troponins." *Am. J. Physiol. Heart Circ. Physiol.* 297.6(2009):H1974-H1983.
Brockes et al. "Studies on Cultured Rat Schwann Cells." *Brain Res.* 165.1(1979):105-118.
Bublil et al. "The EGF Receptor Family: Spearheading a Merger of Signaling and Therapeutics." *Curr. Opin. Cell Biol.* 19.2(2007):124-134.
Buonanno et al. "Neuregulin and ErbB Receptor Signaling Pathways in the Nervous System." *Curr. Opin. Neurobiol.* 11.3(2001):287-296.
Burden et al. "Neuregulins and Their Receptors: A Versatile Signaling Module in Organogenesis and Oncogenesis." *Neuron.* 18.6(1997):847-855.
Busfield et al. "Characterization of a Neuregulin-Related Gene, *Don-1*, That is Highly Expressed in Restricted Regions of the Cerebellum and Hippocampus." *Mol. Cell. Biol.* 17.7(1997):4007-4014.
Cannella et al. "The Neuregulin, Glial Growth Factor 2, Diminishes Autoimmune Demyelination and Enhances Remyelination in a Chronic Relapsing Model for Multiple Sclerosis." *PNAS.* 95.17(1998):10100-10105.
Carraway et al. "Neuregulin-2, a New Ligand of ErbB3/ErbB4-Receptor Tyrosine Kinases." *Nature.* 387(1997):512-516.
Chang et al. "Ligands for ErbB-Family Receptors Encoded by a Neuregulin-Like Gene." *Nature.* 387(1997):509-512.
Chen et al. "Expression of Multiple Neuregulin Transcripts in Postnatal Rat Brains." *J. Comp. Neurol.* 349.3(1994):389-400.
Cohn et al. "A Dose-Dependent Increase in Mortality With Vesnarinone Among Patients With Severe Heart Failure." *N. Engl. J. Med.* 339(1998):1810-1816.
Corfas et al. "Differential Expression of ARIA Isoforms in the Rat Brain." *Neuron.* 14.1(1995):103-115.
Eisen et al. "Sorafenib for Older Patients With Renal Cell Carcinoma: Subset Analysis From a Randomized Trial." *J. Natl. Cancer Inst.* 100.20(2008):1454-1463.
Eldridge et al. "Differentiation of Axon-Related Schwann Cells in Vitro." *J. Cell. Biol.* 105(1987):1023-1034.
Falls et al. "ARIA, a Protein That Stimulates Acetylcholine Receptor Syntehsis, is a Member of the Neu Ligand Family." *Cell.* 72.5(1993):801-813.

(Continued)

*Primary Examiner* — Gregory S Emch
(74) *Attorney, Agent, or Firm* — Mintz Levin Cohn Ferris Glovsky and Popeo, P.C.; Shovon Ashraf

(57) ABSTRACT

The present invention relates to administering glial growth factor 2 (GGF2) to a patient in need thereof, to achieve serum levels of GGF2 within a desired therapeutic window determined based on the disease or disorder afflicting the patient. In a particular embodiment, the patient is suffering from a disease or disorder associated with reduced levels of myelination and the GGF2 is administered to promote myelination in the patient.

13 Claims, 15 Drawing Sheets

(56) References Cited

OTHER PUBLICATIONS

Falls. "Neuregulins: Functions, Forms, and Signaling Strategies." *Exp. Cell Res.* 284.1(2003):14-30.
Ferguson et al. "Extracellular Domains Drive Homo- But not Hetero-Dimerization of erbB Receptors." *EMBO. J.* 19.17(2000):4632-4643.
Fukazawa et al. "Neuregulin-1 Protects Ventricular Myocytes From Anthracycline-Induced Apoptosis via erbB4-Dependent Activation of PI3-Kinase/Akt." *J. Mol. Cell Cardiol.* 35.12(2003):1473-1479.
Gassmann et al. "Aberrant Neural and Cardiac Development in Mice Lacking the ErbB4 Neuregulin Receptor." *Nature.* 378.6555(1995):390-394.
GenBank Accession No. AB005060, Nov. 14, 1997.
Goodearl et al. "Purification of Multiple Forms of Glial Growth Factor." *J. Biol. Chem.* 268.24(1993):18095-18102.
Heldin. "Dinnerization of Cell Surface Receptors in Signal Transduction." *Cell.* 80.2(1995):213-223.
Higashiyama et al. "A Novel Brain-Derived Member of the Epidermal Growth Factor Family That Interacts With ErbB3 and ErbB4." *J. Biochem.* 122.3(1997):675-680.
Hijazi et al. "NRG-3 in Human Breast Cancers: Activation of Multiple erbB Family Proteins." *Int. J. Oncol.* 13.5(1998):1061-1067.
Holmes et al. "Identification of Heregulin, A Specific Activator of p185erbB2." *Science.* 256(1992):1205-1210.
Honegger et al. "Evidence for Epidermal Growth Factor (EGF)-Induced Intermolecular Autophosphorylation of the EGF Receptors in Living Cells." *Mol. Cell. Biol.* 10.8(1990):4035-4044.
Hubbard et al. "Autoregulatory Mechanisms in Protein-Tyrosine Kinases." *J. Biol. Chem.* 273.20(1998):11987-11990.
Huijbregts et al. "Hypertrophic Neuropathies and Malignant Peripheral Nerve Sheath Tumors in Transgenic Mice Overexpressing Glial Growth Factor β3 in Myelinating Schwann Cells." *J. Neurosci.* 23.19(2003):7269-7280.
Hynes et al. "ErbB Receptors and Signaling Pathways in Cancer." *Curr. Opin. Cell Biol.* 21.2(2009):177-184.
Iaci et al. "Glial Growth Factor 2 Promotes Functional Recovery With Treatment Initiated Up to 7 Days After Permanent Focal Ischemic Stroke." *Neuropharmacol.* 59.7-8(2010):640-649.
Kastin et al. "Neuregulin-1-β1 Enters Brain and Spinal Cord by Receptor-Mediated Transport." *J. Neurochem.* 88.4(2004):965-970.
Kramer et al. "Neuregulins With an Ig-Like Domain are Essential for Mouse Myocardial and Neuronal Development." *PNAS.* 93.10(1996):4833-4838.
Lee et al. "Requirement for Neuregulin Receptor erbB2 in Neural and Cardiac Development." *Nature.* 378.6555(1995):394-398.
Lemke. "Neuregulins in Development." *Mol. Cell. Neurosci.* 7.4(1996):247-262.
Lemmon et al. "Regulation of Signal Transduction and Signal Diversity by Receptor Oligomerization." *Trends Biochem. Sci.* 19.11(1994):459-463.
Liu et al. "Neuregulin-1/erbB-Activation Improves Cardiac Function and Survival in Models of Ischemic, Dilated, and Viral Cardiomyopathy." *J. Am. Coll. Cardiol.* 48.7(2006):1438-1447.
Marchionni et al. "Glial Growth Factors are Alternatively Spliced erbB2 Ligands Expressed in the Nervous System." *Nature.* 362(1993):312-318.
Maurel et al. "Axonal Regulation of Schwann Cell Proliferation and Survival and the Initial Events of Myelination Requires PI 3-Kinase Activity." *J. Neurosci.* 20.12(2000):4635-4645.
Meyer et al. "Distinct Isoforms of Neuregulin are Expressed in Mesenchymal and Neuronal Cells During Mouse Development." *PNAS.* 91.3(1994):1064-1068.
Meyer et al. "Isofornn-Specific Expression and Function of Neuregulin." *Development.* 124(1997):3575-3586.
Meyer et al. "Multiple Essential Functions of Neuregulin in Development." *Nature.* 378(1995):386-390.
Minghetti et al. "Glial Growth Factors I-III are Specific Mitogens for Glial Cells." *J. Neurosci. Res.* 43.6(1996):684-693.
Nagata et al. "Solution Structure of the Epidermal Growth Factor-Like Domain of Heregulin-α, a Ligand for p180erb*B*-4." *EMBO J.*13.15(1994):3517-3523.
Ogata et al. "Opposing Extracellular Signal-Regulated Kinase and Akt Pathways Control Schwann Cell Myelination." *J. Neurosci.* 24.30(2004):6724-6732.
Orr-Urtreger et al. "Neural Expression and Chromosomal Mapping of Neu Differentiation Factor to 8p12-p21." *PNAS.* 90.5(1993):1867-1871.
Özcelik et al. "Conditional Mutation of the ErbB2 (HER2) Receptor in Cardiomyocytes Leads to Dilated Cardiomyopathy." *PNAS.* 99.13(2002):8880-8885.
Parkinson et al. "c-Jun is a Negative Regulator of Myelination." *J. Cell. Biol.* 181.4(2008):625-637.
Peles et al. "Isolation of the Neu/HER-2 Stimulatory Ligand: A 44 kd Glycoprotein That Induces Differentiation of Mammary Tumor Cells." *Cell.* 69.1(1992):205-216.
Peles et al. "Neu and its Ligands: From an Oncogene to Neural Factors." *BioEssays.* 15.12(1993):815-824.
Pinkas-Kramarski et al. "Brain Neurons and Glial Cells Express Neu Differentiation Factor/Heregulin: A Survival Factor for Astrocytes." *PNAS.* 91.20(1994):9387-9391.
Pinkas-Kramarski et al. "Differential Expression of NDF/Neuregulin Receptors ErbB-3 and ErbB-4 and Involvement in Inhibition of Neuronal Differentiation." *Oncogene.* 15(1997):2803-2815.
Pinkas-Kramarski et al. "ErB Tyrosine Kinases and the Two Neuregulin Families Constitute a Ligand-Receptor Network." *Mol. Cell. Biol.* 18.10(1998):6090-6101.
Sawyer et al. "Neuregulin-1β for the Treatment of Systolic Heart Failure." *J. Mol. Cell Cardiol.* 51.4(2011):501-505.
Solvd Investigators. "Effect of Enalapril on Mortality and the Development of Heart Failure in Asymptomatic Patients With Reduced Left Ventricular Ejection Fractions." *N. Engl. J. Med.* 327.10(1992):685-691.
Stewart et al. "More 'Malignant' Than Cancer? Five-Year Survival Following a First Admission for Heart Failure." *Eur. J. Heart Fail.* 3.3(2001):315-322.
Sutherland et al. "Neuroprotection for Ischaemic Stroke: Translation From the Bench to the Bedside." *Int. J. Stroke.* 7.5(2012):407-418.
Syed et al. "Soluble Neuregulin-1 has Bifunctional, Concentration-Dependent Effects on Schwann Cell Myelination." *J. Neurosci.* 30.17(2010):6122-6131.
Wen et al. "Neu Differentiation Factor: A Transmembrane Glycoprotein Containing an EGF Domain and an Immunoglobulin Homology Unit." *Cell.* 69.3(1992):559-572.
Xu et al. "Extended Therapeutic Window and Functional Recovery After Intraarterial Administration of Neuregulin-1 After Focal Ischemic Stroke." *J. Cerebral Blood Flow Metab.* 26(2005):527-535.
Zanazzi et al. "Glial Growth Factor/Neuregulin Inhibits Schwann Cell Myelination and Induces Demyelination." *J. Cell. Biol.* 152.6(2001):1289-1300.
Zhang et al. "Neuregulin-3 (NRG3): A Novel Neural Tissue-Enriched Protein That Binds and Activates ErbB4." *PNAS.* 94.18(1997):9562-9567.
Zhao et al. "Neuregulins Promote Survival and Growth of Cardiac Myocytes: Persistence of ErbB2 and ErbB4 Expression in Neonatal and Adult Ventricular Myocytes." *J. Biol. Chem.* 273.17(1998):10261-10269.
Awale, Suresh et al., "Identification of Arctigenin as an Antitumor Agent Having the Ability to Eliminate the Tolerance of Cancer Cells to Nutrient Starvation,"Cancer Res., vol. 66(3):1751-1757 (2006).
Barrett, Stephen D. et al., "The discovery of the benzhydroxamate MEK inhibitors CI-1040 and PD 0325901," Bioorganic & Medicinal Chemistry Letters, vol. 18:6501-6504 (2008).
Bennett, Brydon L. et al., "SP600125, an anthrapyrazolone inhibitor of Jun N-terminal kinase," PNAS, vol. 98 (24):13681-13686 (2001).
Duncia, John V. et al., "MEK Inhibitors: The Chemistry and Biological Activity of U0126, its Analogs, and Cyclization Products," Bioorganic & Medicinal Chemistry Letters, vol. 8:2839-2844 (1998).
Lee, John C. et al., "A protein kinase involved in the regulation of inflammatory cytokine biosynthesis," Nature, vol. 372:739-746 (1994).

(56) References Cited

OTHER PUBLICATIONS

Monia, Brett P. et al., "Antitumor activity of a phosphorothioate antisense oligodeoxynucleotide targeted against C-raf kinase," Nature Medicine, vol. 2(6):668-675 (1996).

Reiners, John J. et al., "PD98059 Is an Equipotent Antagonist of the Aryl Hydrocarbon Receptor and Inhibitor of Mitogen-Activated Protein Kinase Kinse," Molecular Pharmacology, vol. 53:438-445 (1998).

* cited by examiner

Fig. 5A

Nucleotide Sequence & Deduced Acid Sequence of GGF2HBS5

```
GGAATTCCTT TTTTTTTTTT TTTTTTTTCTT NNTTTTTTTT TGCCCTTATA CCTCTTCGCC        60

TTTCTGTGGT TCCATCCACT TCTTCCCCCT CCTCCTCCCA TAAACAACTC TCCTACCCCT       120

GCACCCCCAA TAAATAAATA AAAGGAGGAG GGCAAGGGGG GAGGAGGAGG AGTGGTGCTG       180

CGAGGGGAAG GAAAAGGGAG GCAGCGCGAG AAGAGCCGGG CAGAGTCCGA ACCGACAGCC       240

AGAAGCCCGC ACGCACCTCG CACC ATG AGA TGG CGA CGC GCC CCG CGC CGC         291
                           Met Arg Trp Arg Arg Ala Pro Arg Arg

TCC GGG CGT CCC GGC CCC CAG CGC CCC GGC TCC GCC GCC CGC                339
Ser Gly Arg Pro Gly Pro Gln Arg Pro Gly Ser Ala Ala Arg

TCG TCG CCG CCG CTG CCA CTA CTG CTG CTG CTG CTG GGG ACC                387
Ser Ser Pro Pro Leu Pro Leu Leu Leu Leu Leu Leu Gly Thr
                                        Val Cys Leu Thr Val
                                                 GGF-II 09

GCG GCC CTG GCG GGG GCG GCC AAC GAG GCG GCT CCC GCG                    435
Ala Ala Leu Ala Pro Gly Ala Ala Asn Glu Ala Ala Pro Ala
Ala Ala Leu Pro Pro

GGG GCC TCG TGC TAC TCG TCC CCG AGC GTG GGA TCG GTG CAG                483
Gly Ala Ser Cys Tyr Ser Ser Pro Ser Val Gly Ser Val Gln
                    Ala Ser Pro Val Ser Val Gly Ser Val Gln
                                            GGF-II 08

GAG CTA GCT CAG CGC GCC GCG GTG GTG ATC GAG GGA AAG GTG CAC CCG        531
Glu Leu Ala Gln Arg Ala Ala Val Val Ile Glu Gly Lys Val His Pro
Glu Leu Val Gln Arg Trp Phe Val Val Ile Glu Gly Lys
            GGF-II 04
```

Fig. 5B

Nucleotide Sequence & Deduced Acid Sequence of GGF2HBS5

```
CAG CGG CAG GGG GCA CTC GAC AGG AAG GCG GCG GCG GCG    579
Gln Arg Gln Gly Ala Leu Asp Arg Lys Ala Ala Ala Ala

GGC GAG GGG GCA GCG TGG GGC GGC GAT CGC GAG CCG CCA GCC GGC    627
Gly Glu Gly Ala Ala Trp Gly Gly Asp Arg Glu Pro Pro Ala Gly

CCA CGG GCG CTG GGG CCC GAG GAG CCG CTC GCC GCC AAC    675
Pro Arg Ala Leu Gly Pro Ala Glu Glu Pro Leu Leu Ala Asn

GGG ACC GTG CCC TCT TGG CCC ACC GCC CCG GTG CCC GCC GGC GAG    723
Gly Thr Val Pro Ser Trp Pro Thr Ala Pro Val Pro Ser Ala Gly Glu

CCC GGG GAG GCG CCC TAT CTG GTG AAG GTG CAC GTG CAG GTG TGG GCG    771
Pro Gly Glu Ala Pro Tyr Leu Val Lys Val His Val Gln Val Trp Ala
                                Lys Val His Glu Val Trp Ala
                                      GGF-II 01 & GGF-II 11

GTG AAA GCC GGG GGC TTG AAG AAG GAC TCG CTG CTC ACC GTG CGC CTG    819
Val Lys Ala Gly Gly Leu Lys Lys Asp Ser Leu Leu Thr Val Arg Leu
Ala Lys                     Asp Leu Leu Leu Xaa Val     Leu
                                  GGF-II 10

GGG ACC TGG GGC CAC CCC GCC TTC CCC TGC TCC TGC GGG AGG CTC AAG GAG    867
Gly Thr Trp Gly His Pro Ala Phe Pro Cys Ser Cys Gly Arg Leu Lys Glu
Gly Ala Trp Gly Pro Pro Ala Phe Pro Val Xaa Tyr
              GGF-II 03

GAC AGC AGG TAC ATC TTC TTC ATG GAG CCC GAC GCC AAC AGC ACC AGC    915
Asp Ser Arg Tyr Ile Phe Phe Met Glu Pro Asp Ala Asn Ser Thr Ser
          Tyr Ile Phe Phe Met Glu Pro Gla Ala Xaa Ser Ser Gly
                                  GGF-II 02
```

Fig. 5C

Nucleotide Sequence & Deduced Acid Sequence of GGF2HBS5

```
CGC GCG CCG GCC TTC CGA GCC TCT TTC CCC CCT CTG GAG ACG GGC    963
Arg Ala Pro Ala Phe Arg Ala Ser Phe Pro Pro Leu Glu Thr Gly

CGG AAC CTC AAG AAG GAG GTC AGC CGG CTG TGC AAG CGG TGC GCC   1011
Arg Asn Leu Lys Lys Glu Val Ser Arg Leu Cys Lys Arg Cys Ala

TTG CCT CCC CAA TTG AAA GAG ATG AAA AGC CAG GAA TCG GCA GGT   1059
Leu Pro Pro Gln Leu Lys Glu Met Lys Ser Gln Glu Ser Ala Gly
                                                    Ala Gly

TCC AAA CTA GTC CTT CGG TGT GAA ACC AGT TCT GAA TAC TCC CTC   1107
Ser Lys Val Leu Arg Cys Glu Thr Ser Ser Glu Tyr Ser Leu
    Leu Val Leu Arg
    GGF-II 06

AGA TTC AAG TGG TTC AAG AAT GGG AAT GAA TTG AAT CGA AAA AAC AAA   1155
Arg Phe Lys Trp Phe Lys Asn Gly Asn Glu Leu Asn Arg Lys Asn Lys

CCA CAA AAT ATC AAG ATA CAA AAA CAG GGG CCA AAG TCA GAA CTT CGC   1203
Pro Gln Asn Ile Lys Ile Gln Lys Gln Gly Pro Lys Ser Glu Leu Arg

ATT AAC AAA GCA TCA CTG GCT GAT TCT GGA GAG TAT ATG TGC AAA GTG   1251
Ile Asn Lys Ala Ser Leu Ala Asp Ser Gly Glu Tyr Met Cys Lys Val
Lys Ala Ser Leu Ala Asp Ser Gly Glu Tyr Met Xaa Lyx
                    GGF-II 12

ATC AGC AAA TTA GGA AAT GAC AGT GCC TCT GCC AAT ATC ACC GTG   1299
Ile Ser Lys Leu Gly Asn Asp Ser Ala Ser Ala Asn Ile Thr Val

GAA TCA AAC GCT ACA TCT ACA TCC ACC ACT GGG ACA AGC CAT CTT GTA   1347
Glu Ser Asn Ala Thr Ser Thr Thr Gly Thr Ser His Leu Val
```

Fig. 5D

Nucleotide Sequence & Deduced Acid Sequence of GGF2HBS5

```
AAA TGT GCG GAG AAG GAG AAA ACT TTC TGT GTG AAT GGA GGG GAG TGC        1395
Lys Cys Ala Glu Lys Glu Lys Thr Phe Cys Val Asn Gly Gly Glu Cys

TTC ATG GTG AAA GAC CTT TCA AAC CCC TCG AGA TAC TTG TGC AAG TGC        1443
Phe Met Val Lys Asp Leu Ser Asn Pro Ser Arg Tyr Leu Cys Lys Cys

CCA AAT GAG TTT ACT GGT GAT CGC TGC CAA AAC TAC GTA ATG GCC AGC        1491
Pro Asn Glu Phe Thr Gly Asp Arg Cys Gln Asn Tyr Val Met Ala Ser

TTC TAC AGT ACG TCC ACT CCC TTT CTG TCT CTG CCT GAA                    1530
Phe Tyr Ser Thr Ser Thr Pro Phe Leu Ser Leu Pro Glu

TAGGAGCATG CTCAGTTGGT GCTGCTTTCT TGTTGCTGCA TCTCCCCTCA GATTCCACCT      1590

AGAGCTAGAT GTGTCTTACC AGATCTAATA TTGACTGCCT CTGCCTGTCG CATGAGAACA      1650

TTAACAAAAG CAATTGTATT ACTTCCTCTG TTCGCGACTA GTTGGCTCTG AGATACTAAT      1710

AGGTGTGTGA GGCTCCGGAT GTTTCTGGAA TTGATATTGA ATGATGTGAT ACAAATTGAT      1770

AGTCAATATC AAGCAGTGAA ATATGATGAA AAAGGCATTT CAAAGTCTCA CTTTTATTGA      1830

TAAAATAAAA ATCATTCTAC TGAACAGTCC ATCTTCTTTA TACAATGACC ACATCCTGAA      1890

AAGGGTGTTG CTAAGCTGTA ACCGATATGC ACTTGAAATG ATGGTAAGTT AATTTTGATT      1950

CAGAATGTGT TATTTGTCAC AAATAAACAT AATAAAAGGA AAAAAAAAAA AAA             2003
```

Fig. 6

EGFL1

| | | | | | | | | | | | | | | | | |
|---|---|---|---|---|---|---|---|---|---|---|---|---|---|---|---|---|
|AGC|CAT|CTT|GTC|AAG|TGT|GCA|GAG|AAG|GAG|AAA|ACT|TTC|TGT|GTG|AAT|48|
|Ser|His|Leu|Val|Lys|Cys|Ala|Glu|Lys|Glu|Lys|Thr|Phe|Cys|Val|Asn| |
|GGA|GGC|GAG|TGC|TTC|ATG|GTG|AAA|GAC|CTT|TCA|AAT|CCC|TCA|AGA|TAC|96|
|Gly|Gly|Glu|Cys|Phe|Met|Val|Lys|Asp|Leu|Ser|Asn|Pro|Ser|Arg|Tyr| |
|TTG|TGC|AAG|TGC|CCA|AAT|GAG|TTT|ACT|GGT|GAT|CGC|TGC|CAA|AAC|TAC|144|
|Leu|Cys|Lys|Cys|Pro|Asn|Glu|Phe|Thr|Gly|Asp|Arg|Cys|Gln|Asn|Tyr| |
|GTA|ATG|GCC|AGC|TTC|TAC|AGT|ACG|TCC|ACT|CCC|TTT|CTG|TCT|CTG|CCT|192|
|Val|Met|Ala|Ser|Phe|Tyr|Ser|Thr|Ser|Thr|Pro|Phe|Leu|Ser|Leu|Pro| |
|GAA|TAG| | | | | | | | | | | | | | |198|
|Glu| | | | | | | | | | | | | | | | |

Fig. 7

EGFL2

```
AGC CAT CTT GTC AAG TGT GCA GAG AAG GAG AAA ACT TTC TGT GTG AAT
Ser His Leu Val Lys Cys Ala Glu Lys Glu Lys Thr Phe Cys Val Asn        48

GGA GGC GAG TGC TTC ATG GTG AAA GAC CTT TCA AAT CCC TCA AGA TAC
Gly Gly Glu Cys Phe Met Val Lys Asp Leu Ser Asn Pro Ser Arg Tyr        96

TTG TGC AAG TGC CAA CCT GGA TTC ACT GGA GCG AGA TGT ACT GAG AAT
Leu Cys Lys Cys Gln Pro Gly Phe Thr Gly Ala Arg Cys Thr Glu Asn       144

GTG CCC ATG AAA GTC CAA ACC CAA GAA AAA GCG GAG GAG CTC TAC TAA
Val Pro Met Lys Val Gln Thr Gln Glu Lys Ala Glu Glu Leu Tyr           192
```

Fig. 8

EGFL3

| | | | | | | | | | | | | | | | |
|---|---|---|---|---|---|---|---|---|---|---|---|---|---|---|---|
| AGC | CAT | CTT | GTC | AAG | TGT | GCA | GAG | AAG | GAG | AAA | ACT | TTC | TGT | GTG | AAT | 48
| Ser | His | Leu | Val | Lys | Cys | Ala | Glu | Lys | Glu | Lys | Thr | Phe | Cys | Val | Asn |

| GGA | GGC | GAG | TGC | TTC | ATG | GTG | AAA | GAC | CTT | TCA | AAT | CCC | TCA | AGA | TAC | 96
| Gly | Gly | Glu | Cys | Phe | Met | Val | Lys | Asp | Leu | Ser | Asn | Pro | Ser | Arg | Tyr |

| TTG | TGC | AAG | TGC | CCA | AAT | GAG | TTT | ACT | GGT | GAT | CGC | TGC | CAA | AAC | TAC | 144
| Leu | Cys | Lys | Cys | Pro | Asn | Glu | Phe | Thr | Gly | Asp | Arg | Cys | Gln | Asn | Tyr |

| GTA | ATG | GCC | AGC | TTC | TAC | AAA | GCG | GAG | GAG | CTC | TAC | TAA | | | | 183
| Val | Met | Ala | Ser | Phe | Tyr | Lys | Ala | Glu | Glu | Leu | Tyr | | | | | |

Fig. 9

EGFL4

| | | | | | | | | | | | | | | | |
|---|---|---|---|---|---|---|---|---|---|---|---|---|---|---|---|
| AGC | CAT | CTT | GTC | AAG | TGT | GCA | GAG | AAG | GAG | AAA | ACT | TTC | TGT | GTG | AAT |
| Ser | His | Leu | Val | Lys | Cys | Ala | Glu | Lys | Glu | Lys | Thr | Phe | Cys | Val | Asn | 48

| GGA | GGC | GAG | TGC | TTC | ATG | GTG | AAA | GAC | CTT | TCA | AAT | CCC | TCA | AGA | TAC |
|---|---|---|---|---|---|---|---|---|---|---|---|---|---|---|---|
| Gly | Gly | Glu | Cys | Phe | Met | Val | Lys | Asp | Leu | Ser | Asn | Pro | Ser | Arg | Tyr | 96

| TTG | TGC | AAG | TGC | CCA | AAT | GAG | TTT | ACT | GGT | GAT | CGC | TGC | CAA | AAC | TAC |
|---|---|---|---|---|---|---|---|---|---|---|---|---|---|---|---|
| Leu | Cys | Lys | Cys | Pro | Asn | Glu | Phe | Thr | Gly | Asp | Arg | Cys | Gln | Asn | Tyr | 144

| GTA | ATG | GCC | AGC | TTC | TAC | AAG | CAT | CTT | GGG | ATT | GAA | TTT | ATG | GAG | AAA |
|---|---|---|---|---|---|---|---|---|---|---|---|---|---|---|---|
| Val | Met | Ala | Ser | Phe | Tyr | Lys | His | Leu | Gly | Ile | Glu | Phe | Met | Glu | Lys | 192

| GCG | GAG | GAG | CTC | TAC | TAA | | | | | | | | | | |
|---|---|---|---|---|---|---|---|---|---|---|---|---|---|---|---|
| Ala | Glu | Glu | Leu | Tyr | | | | | | | | | | | | 210

Fig. 10

EGFL5

| | | | | | | | | | | | | | | | | |
|---|---|---|---|---|---|---|---|---|---|---|---|---|---|---|---|---|
| AGC | CAT | CTT | GTC | AAG | TGT | GCA | GAG | AAG | GAG | AAA | ACT | TTC | TGT | GTG | AAT | 48 |
| Ser | His | Leu | Val | Lys | Cys | Ala | Glu | Lys | Glu | Lys | Thr | Phe | Cys | Val | Asn | |
| GGA | GGC | GAG | TGC | TTC | ATG | GTG | AAA | GAC | CTT | TCA | AAT | CCC | TCA | AGA | TAC | 96 |
| Gly | Gly | Glu | Cys | Phe | Met | Val | Lys | Asp | Leu | Ser | Asn | Pro | Ser | Arg | Tyr | |
| TTG | TGC | AAG | TGC | CAA | CCT | GGA | TTC | ACT | GGA | GCG | AGA | TGT | ACT | GAG | AAT | 144 |
| Leu | Cys | Lys | Cys | Gln | Pro | Gly | Phe | Thr | Gly | Ala | Arg | Cys | Thr | Glu | Asn | |
| GTG | CCC | ATG | AAA | GTC | CAA | ACC | CAA | GAA | AAG | TGC | CCA | AAT | GAG | TTT | ACT | 192 |
| Val | Pro | Met | Lys | Val | Gln | Thr | Gln | Glu | Lys | Cys | Pro | Asn | Glu | Phe | Thr | |
| GGT | GAT | CGC | TGC | CAA | AAC | TAC | GTA | ATG | GCC | AGC | TTC | TAC | AGT | ACG | TCC | 240 |
| Gly | Asp | Arg | Cys | Gln | Asn | Tyr | Val | Met | Ala | Ser | Phe | Tyr | Ser | Thr | Ser | |
| ACT | CCC | TTT | CTG | TCT | CTG | CCT | GAA | TAG | | | | | | | | 267 |
| Thr | Pro | Phe | Leu | Ser | Leu | Pro | Glu | | | | | | | | | |

Fig. 11

EGFL6

```
AGC CAT CTT GTC AAG TGT GCA GAG AAA GAG AAA ACT TTC TGT GTG AAT      48
Ser His Leu Val Lys Cys Ala Glu Lys Glu Lys Thr Phe Cys Val Asn

GGA GGC GAG TGC TTC ATG GTG AAA GAC CTT TCA AAT CCC TCA AGA TAC      96
Gly Gly Glu Cys Phe Met Val Lys Asp Leu Ser Asn Pro Ser Arg Tyr

TTG TGC AAG TGC CAA CCT GGA TTC ACT GGA GCG AGA TGT ACT GAG AAT     144
Leu Cys Lys Cys Gln Pro Gly Phe Thr Gly Ala Arg Cys Thr Glu Asn

GTG CCC ATG AAA GTC CAA ACC CAA GAA AAG TGC CCA AAT GAG TTT ACT     192
Val Pro Met Lys Val Gln Thr Gln Glu Lys Cys Pro Asn Glu Phe Thr

GGT GAT CGC TGC CAA AAC TAC GTA ATG GCC AGC TTC TAC AAA GCG GAG     240
Gly Asp Arg Cys Gln Asn Tyr Val Met Ala Ser Phe Tyr Lys Ala Glu

GAG CTC TAC TAA                                                      252
Glu Leu Tyr
```

| RNA | | | | | | | |
|---|---|---|---|---|---|---|---|
| Size | 2224 bp | | | | | | |
| TRANSCRIPTS | number of transcripts | 9 | type | messenger | | | |
| text | other alternative forms | | | | | | |
| identification | major | type | bp | product | | | |
| | | | | kDa | AA | expressed in | author |
| HRG-gamma, NRG1 type 1 | - | splicing | 1651 | - | 211 | - | Holmes |
| GGF2, NRG1 type 2 | - <br> soluble form | splicing | 1986 | - | 422 | nervous system, skeletal muscle | Marchionni, Holmes |
| SMDF, NRG1 type3 | - <br> a C-terminal EGF-like domain and a unique N-terminal sequence which lacks an Ig-like domain, cysteine-rich domain (CRD) | splicing | 1860 | 31,6 | 296 | in the nervous system spinal cord, motoneuron, fetal lung, liver, kidney | Holmes, Michailov |
| HRG-alpha, NRG1 type1 | yes | splicing | 2224 | 70.2 | 640 | breast, ovary, testis, prostate, heart, muscle | Holmes, Michailov |
| HRG-beta 1, NRG1 type 1 | - | splicing | 2199 | - | 645 | neuronal | Holmes |
| HRG-beta 2, NRG1 type 1 | - | splicing | 2490 | - | 637 | - | Holmes |
| HRG-beta 3, NRG1 type 1 | - <br> may be a nuclear isoform | splicing | 1715 | - | 241 | brain spinal cord | Marchionni, Holmes |
| HRG-NDF43, NRG1 type 1 | - | splicing | 1793 | - | 462 | - | Wen, Holmes |
| GGF, NRG1 type 2 | - <br> immunoglobulin-like and EGF-like domain and a kringle-like sequence | splicing | 1199 | - | 241 | nervous system, skeletal muscle | Marchionni, Holmes |

Figure 12

METHOD FOR ACHIEVING DESIRED GLIAL GROWTH FACTOR 2 PLASMA LEVELS

CROSS REFERENCE TO RELATED APPLICATIONS

This application is a continuation of U.S. application Ser. No. 12/380,760, filed on Mar. 2, 2009, now U.S. Pat. No. 8,410,050 and claims priority under 35 USC §119(e) from U.S. Provisional Application Ser. No. 61/067,589, filed Feb. 29, 2008, the contents of which are each herein incorporated by reference in their entirety.

GOVERNMENT SUPPORT

The invention was made with U.S. Government Support under National Institutes of Health (NIH) Grant No. RO1-NS45939-01. The United States Government has certain rights in the invention.

FIELD OF THE INVENTION

The present invention relates to administering glial growth factor 2 (GGF2) to a patient in need thereof, to achieve serum levels of GGF2 within a desired therapeutic window determined based on the disease or disorder afflicting the patient.

BACKGROUND

Neuregulins (NRGs) and NRG receptors comprise a growth factor-receptor tyrosine kinase system for cell-cell signaling that is involved in organogenesis in nerve, muscle, epithelia, and other tissues (Lemke, Mol. Cell. Neurosci. 7:247-262, 1996; Burden et al., Neuron 18:847-855, 1997). The NRG family consists of three genes that encode numerous ligands containing epidermal growth factor (EGF)-like, immunoglobulin (Ig), and other recognizable domains. Numerous secreted and membrane-attached isoforms function as ligands in this signaling system. The receptors for NRGs are all members of the EGF receptor (EGFR) family, and include EGFR (or ErbB1), ErbB2, ErbB3, and ErbB4, also known as HER1 through HER4, respectively, in humans (Meyer et al., Development 124:3575-3586, 1997; Orr-Urtreger et al., Proc. Natl. Acad. Sci. USA 90: 1867-71, 1993; Marchionni et al., Nature 362:312-8, 1993; Chen et al., J. Comp. Neurol. 349:389-400, 1994; Corfas et al., Neuron 14:103-115, 1995; Meyer et al., Proc. Natl. Acad. Sci. USA 91:1064-1068, 1994; and Pinkas-Kramarski et al., Oncogene 15:2803-2815, 1997).

The three NRG genes, Nrg-1, Nrg-2, and Nrg-3, map to distinct chromosomal loci (Pinkas-Kramarski et al., Proc. Natl. Acad. Sci. USA 91:9387-91, 1994; Carraway et al., Nature 387:512-516, 1997; Chang et al., Nature 387:509-511, 1997; and Zhang et al., Proc. Natl. Acad. Sci. USA 94:9562-9567, 1997), and collectively encode a diverse array of NRG proteins. The most thoroughly studied to date are the gene products of Nrg-1, which comprise a group of approximately 15 distinct structurally-related isoforms (Lemke, Mol. Cell. Neurosci. 7:247-262, 1996 and Peles and Yarden, BioEssays 15:815-824, 1993). The first-identified isoforms of NRG-1 included Neu Differentiation Factor (NDF; Peles et al., Cell 69, 205-216, 1992 and Wen et al., Cell 69, 559-572, 1992), Heregulin (HRG; Holmes et al., Science 256:1205-1210, 1992), Acetylcholine Receptor Inducing Activity (ARIA; Falls et al., Cell 72:801-815, 1993), and the glial growth factors GGF1, GGF2, and GGF3 (Marchionni et al. Nature 362:312-8, 1993).

The Nrg-2 gene was identified by homology cloning (Chang et al., Nature 387:509-512, 1997; Carraway et al., Nature 387:512-516, 1997; and Higashiyama et al., J. Biochem. 122:675-680, 1997) and through genomic approaches (Busfield et al., Mol. Cell. Biol. 17:4007-4014, 1997). NRG-2 cDNAs are also known as Neural- and Thymus-Derived Activator of ErbB Kinases (NTAK; Genbank Accession No. AB005060), Divergent of Neuregulin (Don-1), and Cerebellum-Derived Growth Factor (CDGF; PCT application WO 97/09425). Experimental evidence shows that cells expressing ErbB4 or the ErbB2/ErbB4 combination are likely to show a particularly robust response to NRG-2 (Pinkas-Kramarski et al., Mol. Cell. Biol. 18:6090-6101, 1998). The Nrg-3 gene product (Zhang et al., supra) is also known to bind and activate ErbB4 receptors (Hijazi et al., Int. J. Oncol. 13:1061-1067, 1998).

An EGF-like domain is present at the core of all forms of NRGs, and is required for binding and activating ErbB receptors. Deduced amino acid sequences of the EGF-like domains encoded in the three genes are approximately 30-40% identical (pairwise comparisons). Moreover, there appear to be at least two sub-forms of EGF-like domains in NRG-1 and NRG-2, which may confer different bioactivities and tissue-specific potencies.

Cellular responses to NRGs are mediated through the NRG receptor tyrosine kinases EGFR, ErbB2, ErbB3, and ErbB4 of the epidermal growth factor receptor family (Busfield et al., 1997, Mol Cell Biol. 17:4007-14; Carraway et al., 1997, Nature 387:512-6; Chang et al., 1997, Nature 387:509-12). High-affinity binding of all NRGs is mediated principally via either ErbB3 or ErbB4 (Ferguson et al., 2000, EMBO J. 19:4632-43). Binding of NRG ligands leads to dimerization with other ErbB subunits and transactivation by phosphorylation on specific tyrosine residues (Honegger et al., 1990, Mol Cell Biol. 10:4035-44; Lemmon and Schlessinger, 1994, Trends Biochem Sci. 19:459-63; Heldin, 1995, Cell. 80:213-23; Hubbard et al., 1998, J Biol Chem. 273:11987-90). In certain experimental settings, nearly all combinations of ErbB receptors appear to be capable of forming dimers in response to the binding of NRG-1 isoforms. ErbB2, however, appears to be a preferred dimerization partner that may play an important role in stabilizing the ligand-receptor complex.

GGF2 has been shown to promote proliferation, differentiation and protection of Schwann cells (Goodearl et al., 1993, J Biol Chem. 268:18095-102; Minghetti et al., 1996 J Neurosci Res. 43:684-93). Expression of NRG-1, ErbB2, and ErbB4 is also necessary for trabeculation of the ventricular myocardium during mouse development (Meyer and Birchmeier 1995, Nature 378:386-90; Gassmann et al., 1995, Nature 378:390-4; Kramer et al., 1996, Proc Natl Acad Sci USA 93:4833-8). GGF2 has also been shown to promote proliferation and protection of cardiomyocyte cells (Zhao et al., 1998, J Biol Chem 273:10261-10269). GGF2-mediated neuroprotection has also been demonstrated in animal models of stroke, although parameters relating to dosing remain undefined.

The present invention advances the use of GGF2 with respect to therapeutic applications by presenting guidance as to methods for GGF2 administration that optimize therapeutic benefit, while limiting adverse effects. The present invention defines target therapeutic windows for GGF2 serum concentration levels that are specified with respect to particular disease conditions.

SUMMARY

The present invention relates to administering GGF2 to a patient in need thereof to achieve a serum plasma level of GGF2 within a target therapeutic window determined to be effective in the treatment of a disease or disorder. In accordance with the present invention, GGF2 may be administered in a pharmaceutical composition.

In accordance with the present invention, a method for avoiding inhibition of Schwann cell myelination following administration of glial growth factor 2 (GGF2) in a subject is presented, said method comprising: providing a subject in need of neuron myelination; providing GGF2 in a pharmaceutically acceptable carrier; administering the GGF2 to the subject; and, determining that the amount of GGF2 is less than the amount that inhibits Schwann cell myelination.

In another embodiment, the present invention relates to a method for promoting myelination in a patient afflicted with a disease or disorder associated with reduced levels of myelination, the method comprising: selecting the patient afflicted with a disease or disorder associated with reduced levels of myelination; administering glial growth factor 2 (GGF2) to the patient in an amount of about 500 ng of GGF2 per kg of body weight; whereby myelination is promoted.

In yet another embodiment, the present invention relates to a method for promoting myelination in a patient afflicted with a disease or disorder associated with reduced levels of myelination, the method comprising: selecting a patient afflicted with a disease or disorder associated with reduced levels of myelination; and, administering glial growth factor 2 (GGF2) to the patient at an amount that achieves a plasma level of about 0.01 nM GGF2.

In a further embodiment, the present invention relates to a method for broadening the therapeutic dose range for GGF2 when GGF2 is used to facilitate myelination, the method comprising: selecting a subject with a disease or disorder associated with reduced levels of myelination; administering GGF2 and a Mek1/Erk pathway inhibitor to the patient, and, whereby GGF2-mediated myelination is occurs at higher doses of GGF2 than would occur in the absence of administering the Mek1/Erk pathway inhibitor.

In another embodiment, the present invention relates to a method for determining if an amount of GGF2 is a therapeutically effective amount for promoting myelination, the method comprising: providing a subject receiving GGF2 therapy; and measuring c-Jun protein levels in the subject, whereby an increase in c-Jun relative to baseline c-Jun levels indicates that the amount of GGF2 is near a maximum threshold of therapeutic efficacy for promoting myelination.

In a particular embodiment of the invention, GGF2 is administered to a mammal using a dosing regimen directed to achieving a narrow target therapeutic window of plasma GGF2 concentrations.

As indicated herein, GGF2 is known to be able to promote proliferation, differentiation and protection of Schwann cells. GGF2 has also been shown to promote remyelination and reduce symptoms in animal models of multiple sclerosis including experimental autoimmune encephalomyelitis. Under some circumstances (e.g., at high concentrations of GGF2), however, GGF2 can prevent myelination of neurons co-cultured with Schwann cells.

The data presented herein demonstrate that GGF2 is indeed capable of promoting myelination of peripheral nerves but teach that precise dosing of GGF2 to a mammal in need thereof is required to achieve the desired GGF2-mediated promoted myelination of peripheral nerves. As taught herein, GGF2 is administered so as to be within a therapeutic window of plasma GGF2 concentrations in order to promote myelination. In the absence of the results presented herein, there is no appreciation of the narrow therapeutic window of plasma GGF2 concentrations required to promote myelination in a mammal in need thereof.

The data presented herein also demonstrate that GGF2 is sufficient to promote myelination and rescue the myelination defect on CRD-Nrg1-deficient axons. At high concentrations, however, GGF2 inhibits myelination in an Erk-dependent manner. The present results demonstrate that GGF2 is capable of both promoting and inhibiting myelination depending on the concentration presented to the Schwann cells.

Accordingly, the present invention relates to the surprising discovery that a hitherto unrealized positive correlation exists between GGF2-mediated PI3-kinase pathway activation and promotion of myelination and a negative correlation exists between GGF2-mediated Mek1/Erk pathway activation and promotion of myelination. Alternatively stated, the present inventors discovered that administration of GGF2 can be finely tuned to promote myelination by assessing activation levels of these pathways. In accordance with the present invention, a target therapeutic window for GGF2 with regard to promoting myelination in a subject is an amount of GGF2 that promotes PI3-kinase pathway activation (assayed, for example, by detecting phosphorylated Akt) in the absence of detectable Mek1/Erk pathway activation (assayed, for example, by detecting phosphorylated Erk).

The formulations and compositions of the present invention exhibit a specific, desired release profile that maximizes the therapeutic effect while minimizing adverse side effects. The desired release profile may be described in terms of the maximum plasma concentration of the drug or active agent ($C_{max}$) and the plasma concentration of the drug or active agent at a specific dosing interval ($C_{tau}$). A ratio of $C_{max}$ to $C_{tau}$ ($C_{max}:C_{tau}$) may be calculated from the observed $C_{max}$ and $C_{tau}$. A dosing interval ($_{tau}$) is the time since the last administration of the drug or active agent. In the present application, the dosing interval ($_{tau}$) may be, for example, twelve (12) hours, in which case $C_{tau}$ is the concentration of the drug or active agent at twelve (12) hours from the last administration.

Additionally, the formulations and compositions of the present invention exhibit a desired release profile that may be described in terms of the maximum plasma concentration of the drug or active agent at steady state ($C_{maxSS}$) and the minimum plasma concentration of the drug or active agent at steady state ($C_{minSS}$). Steady state is observed when the rate of administration (absorption) is equal to the rate of elimination of the drug or active agent. A ratio of $C_{maxSS}$ to $C_{minSS}$ ($C_{maxSS}:C_{minSS}$) may be calculated from the observed $C_{maxSS}$ and $C_{minSS}$. In addition, the formulations and compositions of the present invention exhibit a desired release profile that may be described in terms of the average maximum plasma concentration of the drug or active agent at steady state ($C_{avSS}$).

In an embodiment of the invention directed to a patient in need of remyelination, target peak serum levels of GGF2 are about 0.01 nM.

In an embodiment of the invention directed to a patient in need of remyelination, target peak serum levels of GGF2 are at or about any of the following values, or range between the following values from about 0.001 to 0.01 ng/ml; 0.01 to 0.1 ng/ml; 0.1 to 1.0 ng/ml; 1.0 to 10 ng/ml; 10 to 100 ng/ml; or 100 to 1000 ng/ml. In a particular embodiment, the target peak serum level is about 1.0 ng/ml.

In an embodiment of the invention directed to a patient who has had a stroke, target peak serum levels of GGF2 are at or about any of the following values, or range between the following values from about 0.00001 to 0.0001 ng/ml; 0.0001 to 0.001 ng/ml; 0.001 to 0.01 ng/ml; 0.001 to 0.01 ng/ml; 0.01 to 0.1 ng/ml; 0.1 to 1.0 ng/ml; 1.0 to 10 ng/ml; 10 to 100 ng/ml; 100 to 1000 ng/ml; 1000 to 10000 ng/ml; or 10000 to 100000 ng/ml. In a particular embodiment, the target peak serum level is about 0.2 micrograms/ml.

In an embodiment of the invention directed to a patient who has neuropathy, target peak serum levels of GGF2 are at or about any of the following values, or range between the following values from about 0.001 to 0.01 ng/ml; 0.01 to 0.1 ng/ml; 0.1 to 1.0 ng/ml; 1.0 to 10 ng/ml; 10 to 100 ng/ml; or 100 to 1000 ng/ml. In a particular embodiment, the target peak serum level is about 6.25 ng/ml.

In an embodiment of the invention directed to a patient who has heart failure, target peak serum levels of GGF2 are at or about any of the following values, or range between the following values from about 0.001 to 0.01 ng/ml; 0.01 to 0.1 ng/ml; 0.1 to 1.0 ng/ml; 1.0 to 10 ng/ml; 10 to 100 ng/ml; or 100 to 1000 ng/ml. In a particular embodiment, the target peak serum level is about 6.8 micrograms/ml.

In accordance with the present invention, pharmaceutical compositions comprising GGF2 may be administered via different routes known to those skilled in the art. Any appropriate route of administration may be employed, for example, intravenous, parenteral, subcutaneous, intramuscular, intracranial, intraorbital, ophthalmic, intraventricular, intracapsular, intraspinal, intracisternal, intraperitoneal, intranasal, aerosol, oral, or topical (e.g., by applying an adhesive patch carrying a formulation capable of crossing the dermis and entering the bloodstream) administration. Oral administration is envisioned to include sustained release oral dosage forms comprising GGF2. A GGF2 pharmaceutical composition, as described herein, can be used to treat individuals affected with neurological disorders wherein said pharmaceutical composition maximizes the therapeutic effect, while minimizing adverse side effects.

In a first embodiment of the present invention, GGF2 is administered to a mammal afflicted with a neurological disorder associated with demyelination, wherein the GGF2 is administered in a dosing regimen to achieve and maintain a narrow target therapeutic window of plasma GGF2 concentrations. As taught herein, precise dosing of GGF2 is necessary in order to achieve serum plasma levels of GGF2 required for therapeutic efficacy with respect to inducing myelination in a subject in need thereof. Examples of demyelinating disorders for which suitable dosing of GGF2 is necessary in order to achieve therapeutic efficacy include Guillain-Barre Syndrome, chronic inflammatory demyelinating polyneuropathy, peripheral demyelination due to traumatic injury, multiple sclerosis, optic neuritis, central demyelination due to traumatic injury, transverse myelitis, progressive multifocal leukoencephalopathy, Devic's disease (neuromyelitis optica), acute disseminated encephalomyelitis, adrenoleukodystrophy and adrenoleukoneuropathy.

In a second embodiment of the present invention, GGF2 is administered to a mammal afflicted with a cardiac muscle disorder, such as congestive heart failure, myocardial infarction, reperfusion injury, chemical, viral or idiopathic cardiotoxicity, arrhythmias, wherein the GGF2 is administered in a dosing regimen to achieve a target therapeutic window of plasma GGF2 concentrations.

In a third embodiment of the present invention, GGF2 is administered to a mammal that has suffered a stroke, spinal cord injury or traumatic brain injury, wherein the GGF2 is administered in a dosing regimen to achieve a target therapeutic window of plasma GGF2 concentrations.

It will be appreciated that for any of the applications detailed herein, GGF2 may be administered in any suitable form, or as a component in a pharmaceutical composition and via any means, all of which are described herein and/or understood in the art.

Accordingly, the present invention is directed to identification of a target therapeutic window with respect to a therapeutically effective plasma level of GGF2. The target therapeutic window varies depending of the disease or disorder afflicting the patient and the desired activity conferred by achieving the appropriate therapeutically effective GGF2 plasma level.

A method for selecting individuals based on presentation of symptoms is also encompassed herein. Also encompassed is a method for selecting individuals based on responsiveness to achieving the therapeutically effective GGF2 plasma level, as indicated for each application, is also encompassed herein.

In addition to the methods of treatment set forth above, the present invention extends to the use of any of the compounds of the invention for the preparation of medicaments or as medicaments that may be administered for such treatments, as well as to such compounds for the treatments disclosed and specified.

The present invention also encompasses a pharmaceutical composition comprising GGF2 or an EGFL domain and a Mek1/Erk pathway inhibitor and its use in the treatment of a patient afflicted with a disease or disorder associated with reduced levels of myelination.

BRIEF DESCRIPTION OF THE DRAWINGS

FIG. 5A-D shows the nucleic and amino acid sequences, designated SEQ ID NOs: 1 and 2, respectively, of full length GGF2.

FIGS. 6-11 show the nucleic and amino acid sequences of epidermal growth factor like (EGFL) domains 1-6. The nucleic and amino acid sequences of the EGFL domains are designated as follows: SEQ ID NOs: 3 and 4 for EGFL domain 1 (FIG. 6); SEQ ID NOs: 5 and 6 for EGFL domain 2 (FIG. 7); SEQ ID NOs: 7 and 8 for EGFL domain 3 (FIG. 8); SEQ ID NOs: 9 and 10 for EGFL domain 4 (FIG. 9); and SEQ ID NOs: 11 and 12 for EGFL domain 5 (FIG. 10); and SEQ ID NOs: 13 and 14 for EGFL domain 6 (FIG. 11).

FIG. 12 shows a table relating to neuregulin nomenclature.

DETAILED DESCRIPTION OF THE INVENTION

Figure 1:
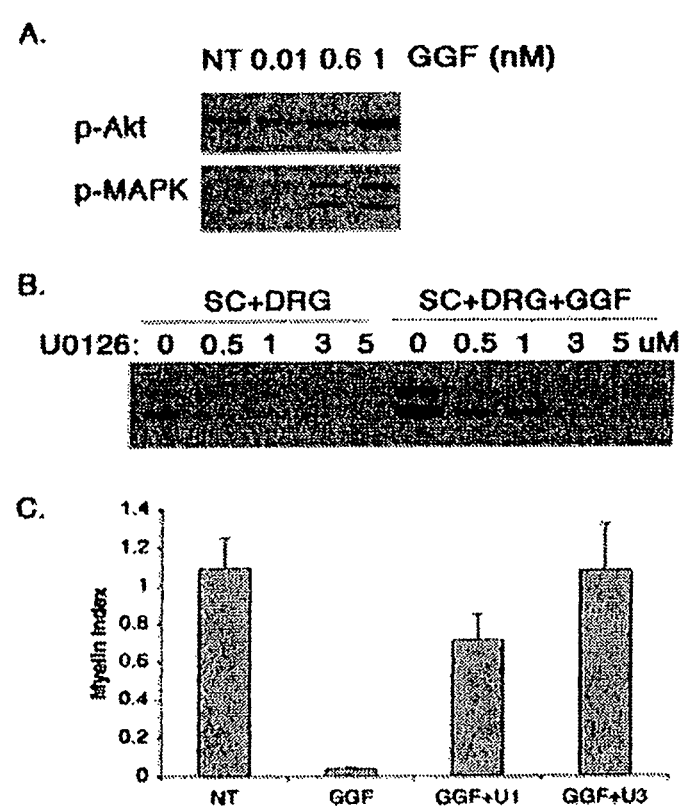
FIG. 1A-C show (A) GGF2-induced Akt and MAPK activation in Schwann cell-DRG neuron co-cultures. Schwann cell-DRG co-cultures under myelinating condition were treated GGF (0.6 μM) and 20 minutes later, Akt and MAPK activation levels were assessed by Western blot analysis. (B) Inhibition of GGF2-induced MAPK activation by U0125. Co-cultures were pretreated with increasing doses of U0125 for 30 minutes then stimulated with GGF2. Control cultures were left untreated. MAPK activation was assessed 20 minutes later. (C) Inhibition of GGF2-induced MAPK activation by U0125 (1 and 3 μM) reverses the inhibitory effect of GGF2 on myelination. Co-cultures were co-treated with GGF2 and U0125 (1 and 3 μM) under myelinating conditions. Ten to twelve days later, cultures were fixed and immunostained for MBP to assess the level of myelination.

The data presented herein demonstrated that in order to promote myelination of peripheral nerves, GGF2 must be administered to a mammal using a dosing regimen directed to achieving a therapeutic window of, e.g., plasma GGF2 concentrations or GGF2 doses.

Definitions

The terms used herein have meanings recognized and known to those of skill in the art, however, for convenience and completeness, particular terms and their meanings are set forth below As used herein "about" means a stated value plus or minus another amount; thereby establishing a range of values. In certain preferred embodiments "about" indicates a range relative to a base (or core or reference) value or amount plus or minus up to 15%, 14%, 13%, 12%, 11%, 10%, 9%, 8%, 7%, 6%, 5%, 4%, 3%, 2%, 1%, 0.75%, 0.5%, 0.25% or 0.1%.

By "epidermal growth factor-like domain" or "EGF-like domain" is meant a polypeptide motif encoded by the NRG-1, NRG-2, or NRG-3 gene that binds to and activates ErbB2, ErbB3, ErbB4, or combinations thereof, and bears a structural similarity to the EGF receptor-binding domain as disclosed in Holmes et al., Science 256:1205-1210, 1992; U.S. Pat. No. 5,530,109; U.S. Pat. No. 5,716,930; U.S. Ser. No. 08/461, 097; Hijazi et al., hit. J. Oncol. 13:1061-1067, 1998; Chang et al., Nature 387:509-512, 1997; Carraway et al., Nature 387: 512-516, 1997; Higashiyama et al., J Biochem. 122:675-680, 1997; and WO 97/09425). See FIGS. 10-15 for nucleic and amino acid sequences of epidermal growth factor like (EGFL) domains 1-6.

By "neuregulin" or "NRG" is meant a polypeptide that is encoded by an NRG-1, NRG-2, or NRG-3 gene or nucleic acid (e.g., a cDNA), and binds to and activates ErbB2, ErbB3, or ErbB4 receptors, or combinations thereof.

By "neuregulin-1," "NRG-1," "heregulin," "GGF2," or "p185erbB2 ligand" is meant a polypeptide that binds directly to or transactivates the ErbB2 receptor and is encoded by the p185erbB2 ligand gene described in U.S. Pat. No. 5,530,109; U.S. Pat. No. 5,716,930; and U.S. Pat. No. 7,037, 888, the contents of each of which are incorporated herein by reference. See FIGS. 9A-D for the nucleic and amino acid sequences of full length GGF2. See FIG. 12 for a table pertaining to neuregulin nomenclature.

Polypeptides encoded by the NRG-1, NRG-2, and NRG-3 genes possess EGF-like domains that allow them to bind to and activate ErbB receptors. Holmes et al. (Science 256: 1205-1210, 1992) have shown that the EGF-like domain alone is sufficient to bind and activate the p185erbB2 receptor. Accordingly, any polypeptide product encoded by the NRG-1, NRG-2, or NRG-3 gene, e.g., a polypeptide having an EGF-like domain encoded by a neuregulin gene or cDNA (e.g., an EGF-like domain, as described in U.S. Pat. No. 5,530,109; U.S. Pat. No. 5,716,930; U.S. Pat. No. 7,037,888, U.S. Pat. No. 7,135,456, and U.S. Pat. No. 7,319,019; or an EGF-like domain as disclosed in WO 97/09425) may be used in the methods of the invention to achieve a therapeutic window wherein an efficacious serum plasma level of GGF2 is achieved.

It must also be noted that as used herein and in the appended claims, the singular forms "a", "an", and "the" include plural reference unless the context clearly dictates otherwise.

Unless defined otherwise, all technical and scientific terms used herein have the same meanings as commonly understood by one of ordinary skill in the art. Although any methods and materials similar or equivalent to those described herein can be used in the practice or testing of embodiments of the present invention, particular methods, devices, and materials are now described.

"Local administration" means direct administration by a non-systemic route at or near the site of affliction or disorder.

The terms "patient" and "subject" are used herein to refer to all animals, including mammals. Examples of patients or subjects include humans, cows, dogs, cats, goats, sheep, and pigs.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention.

The term "prodrug" refers to compounds that are rapidly transformed in vivo to yield the parent compounds of the above formula, for example, by hydrolysis in blood. A thorough discussion is provided in T. Higuchi and V. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference.

The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, tetramethylammonium, tetramethylammonium, methylamine, dimethylamine, trimethylamine, triethylamine, ethylamine, and the like. (See, for example, S. M. Barge et al., "Pharmaceutical Salts," J. Pharm. Sci., 1977, 66:1-19 which is incorporated herein by reference).

A "therapeutically effective amount" is an amount sufficient to decrease the symptoms associated with a medical condition or infirmity, to normalize body functions in disease or disorders that result in impairment of specific bodily functions, or to provide improvement in one or more of the clinically measured parameters of a disease. Preferably, improvement in symptoms associated with the disease associated with a demyelinating disease, for example, including walking speed, lower extremity muscle tone, lower extremity muscle strength, or spasticity. As related to the present application, a therapeutically effective amount is an amount sufficient to reduce the pain or spasticity associated with the neurological disorder being treated, or an amount sufficient to result in improvement of sexual, bladder or bowel function in subjects having a neurological disorder which impairs nerve conduction; or which hinders normal sexual, bladder or bowel functions.

"Treatment" refers to the administration of medicine or the performance of medical procedures with respect to a patient, to ameliorate the clinical condition of the patient, including a decreased duration of illness or severity of illness, or subjective improvement in the quality of life of the patient or a prolonged survival of the patient.

As used herein, the term "target therapeutic window" refers to the dose range or serum concentration range that achieves the desired therapeutic results. With regard to GGF2, in a particular embodiment, the target therapeutic window refers to an amount of GGF2 sufficient to induce Schwann cell myelination in a subject, which amount is less than the amount sufficient to inhibit myelination in a subject. In a surprising discovery, the present inventors identified the target therapeutic window for GGF2 with respect to its ability to promote myelination by determining the relative levels of PI3-kinase pathway activation and Mek1/Erk pathway activation. More particularly, the present inventors discovered the hitherto unrealized positive correlation between GGF2-mediated PI3-kinase pathway activation and promotion of myelination and a negative correlation between GGF2-mediated Mek1/Erk pathway activation and promotion of myelination. Alternatively stated, the present inventors discovered that administration of GGF2 can be finely tuned to promote myelination by assessing activation levels of these pathways. A target therapeutic window for GGF2 with regard to promoting myelination in a subject is defined as an amount of GGF2 that promotes PI3-kinase pathway activation (assayed, for example, by detecting phosphorylated Akt) in the absence of detectable Mek1/Erk pathway activation (assayed, for example, by detecting phosphorylated Erk). Detection of phosphorylated Akt and phosphorylated Erk can be achieved using standard assays known in the art, including ELISA, Western (immuno) blot, immunocytochemistry, in vitro kinase assay, LC/MS (liquid chromatography/mass spectrometry), MaldiTOF MS (Matrix Assisted Laser Desorption/Ionization-Time of Flight mass spectrometry) or other protein systems known to the field such as Luminex One skilled in the art would appreciate that other intracellular markers of PI3-kinase pathway activation and Mek1/Erk pathway activation are known and are used in accordance with the present invention. In accordance with the present invention, other indicators of PI3-kinase pathway activation and Mek1/Erk pathway activation can be used to determine the therapeutic window in which GGF2 promotes myelination.

In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

"MAP Kinase Inhibitors"

A non-limiting list of MAP kinase inhibitors that may be used in the present invention includes: Arctigenin, which potently inhibits the activity of MKK1 in vitro with an IC50 value of 1 nM and thus inhibits the phosphorylation and activation of MAP kinases ERK1/2, p38 kinase and JNK and their activities in Raw264.7 cells treated with LPS; PD 98059, which is a potent, selective and cell-permeable inhibitor of MAP kinase-kinase (also known as MAPK/ERK kinase or MEK) that inhibits phosphorylation of MAP kinase by MAP kinase-kinase but does not inhibit MAP kinase itself. The IC50 values for PD 98059-induced effects are in the 1-20 µM range for many assays; SB202190, which is a highly selective, potent and cell permeable inhibitor of p38 MAP kinases that binds within the ATP pocket of the active kinase with a Kd of 38 nM as measured in recombinant human p38 and selectively inhibits the p38alpha and beta isoforms (IC50 values are 50 and 100 nM for p38alpha/SAPK2alpha and p38beta2/SAPK2beta respectively); SB203580, which is a highly selective and cell permeable inhibitor of p38 mitogen-activated protein kinase with IC50 values of 50 and 500 nM for p38/SAPK2a and p38/SAPK2b respectively and also inhibits the phosphoinositide-dependent protein kinase 1 (PDK1) at 10-fold higher concentrations (IC50~3-5 µM) (Displays 100-500-fold selectivity over Lck, GSK3b and Akt/PKB); SL 327, which is a selective inhibitor of MEK1 and MEK2 with IC50 values of 180 and 220 nM, respectively. It blocks hippocampal LTP in vitro and is brain penetrant in vivo, blocking fear conditioning and learning in rats, and producing neuroprotection in mice, following systemic administration; SP600125, which is a selective inhibitor of c-Jun N-terminal kinase (JNK). It competitively and reversibly inhibits JNK1, 2 and 3 (IC50=40-90 nM) and has been shown to have less inhibitory potency on ERK2, p38b and a range of other kinases and is known to be active in vivo; and U0126, which is a selective inhibitor of the mitogen-activated protein kinase kinases, MEK-1 and MEK-2, with a 100-fold higher potency than PD 98059 and is a weak inhibitor of PKC, Raf, ERK, JNK, MEKK, MKK-3, MKK-4/SEK, MKK-6, Ab1, Cdk2 and Cdk4 and inhibits AP-1 transactivation in cell-based reporter assays.

Other inhibitors that are currently in FDA Phase trial include the farnesyl transferase inhibitors (FTIs). Zarnestra® (R115777, tipifarnib), for example, is the FTI that is furthest along in development. A phase II trial of patients with previously treated metastatic breast cancer tested two different dosing schedules: continuous and intermittent. The objective response rates in the 2 groups were 10% and 14%, with an additional 15% and 9% who had stable disease for at least 6 months. The major side effects observed were bone marrow suppression and neuropathy, both of which were less in the intermittent dosing group than the continuous. Several phase I studies of zarnestra and other FTIs have been performed in combination with cytotoxic chemotherapy and have demonstrated the safety of these combination regimens. Phase II trials in breast cancer are underway, including one using zarnestra in combination with an aromatase inhibitor. FDA approval for zarnestra use in acute myeloid leukemia (AML) is pending phase III data, as the FDA committee voted against accelerated approval for zarnestra based on data from a single-armed phase II trial.

With regard to Zarnestra®, for Phase I clinical trials, Zarnestra® is administered at 400 mg administered orally twice daily for two weeks; for Phase II clinical trials, Zarnestra® is administered at 300 mg administered orally twice daily for the first 21 days of each 28-day cycle; for Phase III clinical trials, Zarnestra® is administered at 600 mg administered orally twice daily for the first 21 days of each 28-day cycle.

The Raf inhibitors comprise another types of inhibitors that are currently in FDA Phase trials. Sorafenib (BAY 43-9006), for example, is the first compound to target not only the Raf/MEK/Erk signaling pathway, but also the VEGFR and PDGFR pathways. In March 2004, sorafenib was granted Fast Track status by the FDA for metastatic renal cell cancer. In April 2005, sorafenib was accepted into the Pilot 1 Program, which is designed for therapies that have been granted FDA Fast Track status and that have the potential to provide significant benefit over existing standard therapy. There are also several large, international, multi-institution phase III clinical studies of sorafenib underway in patients with advanced stage primary cancers of the kidney and liver, as well as metastatic melanoma.

With regard to Sorafenib, Phase I clinical trials tested two dose levels: Dose Level 1: 200 mg of Sorafenib by mouth twice a day for a 3 week cycle or Dose Level 2: 400 mg of Sorafenib by mouth twice a day for a 3 week cycle.

The results of a planned interim analysis of an ongoing phase III trial in patients with advanced kidney cancer were recently presented (Escudier et al. J Natl Cancer Inst. 2008 100:1454-63; the contents of which are incorporated herein in their entirety). Among 769 analyzed patients, progression-free survival (PFS) was doubled to a median value of 24 weeks with sorafenib, compared to 12 weeks with placebo. The benefits from sorafenib were observed in all patient subgroups, regardless of age, duration of disease, or prior therapies. Disease control was achieved in 80% of patients who received sorafenib: 78% had stable disease (compared to 55% in the placebo arm) and 2% had partial response (compared to none in the placebo arm). The 12-week progression-free rate was 79% for sorafenib vs. 50% for placebo. Furthermore, sorafenib was very well tolerated in 768 patients, and the most common side effects were hypertension, fatigue, diarrhea, and rash, including a rash on the hand and foot (hand and foot syndrome). Phase II efficacy trials are studying sorafenib as a single agent in advanced lung, breast, and other cancers. Phase I/II clinical trials are investigating sorafenib in combination with a range of standard chemotherapeutics and other anticancer agents.

ISIS 5132 is another raf inhibitor that has shown acceptable toxicity in phase I studies. Phase II studies are now underway in a variety of cancer types.

Other inhibitors that are currently in FDA Phase trial include the MEK inhibitors. CI-1040, for example, is an oral, selective small-molecule inhibitor of MEK 1-2. Animal and culture studies have shown activity of this agent in breast cancer cell lines. Phase I studies have found mild gastrointestinal and skin side effects. Unfortunately, a phase II study in 67 patients with 4 different tumor types (advanced colorectal, NSCLC, breast, and pancreatic cancer) found no responses, although CI-1040 treatment was well tolerated.

PD 0325901, a second generation MEK inhibitor, has recently entered clinical development and appears to have noticeably better pharmacologic properties compared to CI-1040, which investigators hope may translate into better anti-cancer efficacy. It has shown some partial response in melanoma patients.

With regard to PD 0325901, Phase I and Phase II clinical trials tested multiple dose levels. Administered orally either once or twice a day; several dosing schedules evaluated; current dosing schedule 5 days on-drug, 2-days off drug for 3 weeks in a 28-day cycle. Doses evaluated ranged from 1 mg once a day to 30 mg twice daily. Clinical trials were prematurely discontinued due to safety concerns, specifically ocular and neurological toxicity presented at 10 mg twice-a-day and higher doses.

It is to be understood that this invention is not limited to the particular molecules, compositions, methodologies or protocols described, as these may vary. It is also to be understood that the terminology used in the description is for the purpose of describing particular embodiments only, and is not intended to limit the scope of the present invention, which is limited only by the appended claims.

Administration: Neuregulins and polypeptides containing EGF-like domains encoded by neuregulin genes may be administered to patients or experimental animals with a pharmaceutically-acceptable diluent, carrier, or excipient, in unit dosage form. Conventional pharmaceutical practice may be employed to provide suitable formulations or compositions to administer such compositions to patients or experimental animals. Any appropriate route of administration may be employed, for example, intravenous, parenteral, subcutaneous, intramuscular, intracranial, intraorbital, ophthalmic, intraventricular, intracapsular, intraspinal, intracisternal, intraperitoneal, intranasal, aerosol, oral, or topical (e.g., by applying an adhesive patch carrying a formulation capable of crossing the dermis and entering the bloodstream) administration. Therapeutic formulations may be in the form of liquid solutions or suspensions; for oral administration, formulations may be in the form of tablets or capsules; and for intranasal formulations, in the form of powders, nasal drops, or aerosols. Any of the above formulations may be in a sustained-release formulation.

Methods well known in the art for making formulations are found in, for example, "Remington's Pharmaceutical Sciences.", which is incorporated herein in its entirety. Formulations for parenteral administration may, for example, contain excipients, sterile water, or saline, polyalkylene glycols such as polyethylene glycol, oils of vegetable origin, or hydrogenated napthalenes. Sustained-release, biocompatible, biodegradable lactide polymer, lactide/glycolide copolymer, or polyoxyethylene-polyoxypropylene copolymers may be used to control the release of the compounds. Other useful parenteral delivery systems for administering molecules of the invention include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Thus, and as stated earlier, the present invention includes within its scope, and extends to, the recited methods of treatment and to the use of such compounds for the preparation of medicaments useful for such methods.

Demyelinating Diseases: Myelin sheaths cover many nerve fibers in the central and peripheral nervous system. The presence of intact myelin sheaths accelerates axonal transmission of neural impulses. Disorders that affect myelin interrupt nerve transmission and disease symptoms may reflect deficits in any part of the nervous system.

Myelin formed by oligodendroglia in the central nervous system (CNS) differs chemically and immunologically from that formed by Schwann cells peripherally. Thus, some myelin disorders (e.g., Guillain-Barré syndrome, chronic inflammatory demyelinating polyneuropathy, and other peripheral nerve polyneuropathies) tend to affect primarily the peripheral nerves, whereas other myelin disorders affect primarily the CNS. The most commonly affected areas in the CNS are the brain, spinal cord, and optic nerves.

Demyelination is often secondary to an infectious, ischemic, metabolic, or hereditary disorder. In primary demyelinating disorders, while the cause or causes are unknown, an autoimmune mechanism is suspected because the disorder sometimes follows a viral infection or viral vaccination.

Demyelination tends to be segmental or patchy, affecting multiple areas simultaneously or sequentially. Remyelination can occur, however, with repair, regeneration, and complete recovery of neural function. Extensive myelin loss, however, is usually followed by axonal degeneration and often cell body degeneration.

Multiple sclerosis (MS) is characterized by disseminated patches of demyelination in the brain and spinal cord. Common symptoms include visual and oculomotor abnormalities, paresthesias, weakness, spasticity, urinary dysfunction, and mild cognitive impairment. Typically, neurologic deficits are multiple, with remissions and exacerbations gradually producing disability.

Diagnosis is by history of remissions and exacerbations plus clinical signs, test results, lesions seen on magnetic resonance imaging (MRI), or other criteria (depending on symptoms) to objectively demonstrate ≥2 separate neurologic abnormalities. Treatment generally includes corticosteroids for acute exacerbations, immunomodulatory drugs to prevent exacerbations, and supportive measures.

In MS, localized areas of demyelination (plaques) occur, with destruction of oligodendroglia, perivascular inflammation, and chemical changes in lipid and protein constituents of myelin in and around the plaques. Axonal damage is possible, but cell bodies and axons tend to be relatively well preserved. Fibrous gliosis develops in plaques that are disseminated throughout the CNS, primarily in white matter, particularly in the lateral and posterior columns (especially in the cervical regions), optic nerves, and periventricular areas. Tracts in the midbrain, pons, and cerebellum are also affected. Gray matter in the cerebrum and spinal cord can be affected, but to a much lesser degree.

Heart Disease

Heart disease is a general term for a number of different diseases which affect the heart. It is the leading cause of death in many industrialized countries, including the United States. The following broad categories of heart disease are presented by way of introduction. Extrinsic cardiomyopathies are cardiomyopathies, wherein the primary pathology lies outside the myocardium. Most cardiomyopathies are extrinsic, because the most common cause of cardiomyopathy is ischemia. Intrinsic cardiomyopathies derive from weakness in the heart muscle that is not due to an identifiable external cause. Cardiovascular disease, on the other hand, refers to any number of specific diseases that affect the heart itself and/or the blood vessel system, especially the veins and arteries leading to and from the heart. Research on disease dimorphism suggests that women who suffer with cardiovascular disease usually suffer from forms that affect the blood vessels while men usually suffer from forms that affect the heart muscle itself. Known or associated causes of cardiovascular disease include diabetes mellitus, hypertension, hyperhomocysteinemia and hypercholesterolemia. Ischaemic heart disease is yet another category of disease of the heart itself, typified by reduced blood supply to the organ.

Hypertensive heart disease is a term used to refer to heart disease caused by high blood pressure, especially localized high blood pressure. Inflammatory heart disease involves inflammation of the heart muscle and/or the tissue surrounding it. Valvular heart disease is any disease process involving one or more valves of the heart. The valves in the right side of the heart are the tricuspid valve and the pulmonic valve and the valves in the left side of the heart are the mitral valve and the aortic valve.

Congestive heart failure, one of the leading causes of death in industrialized nations, results from an increased workload on the heart and a progressive decrease in its pumping ability. It can result from any structural or functional cardiac disorder that impairs the ability of the heart to fill with or pump a sufficient amount of blood through the body. Initially, the increased workload that results from high blood pressure or loss of contractile tissue induces compensatory cardiomyocyte hypertrophy and thickening of the left ventricular wall, thereby enhancing contractility and maintaining cardiac function. Over time, however, the left ventricular chamber dilates, systolic pump function deteriorates, cardiomyocytes undergo apoptotic cell death, and myocardial function progressively deteriorates.

Factors that underlie congestive heart failure include high blood pressure, ischemic heart disease, exposure to cardiotoxic compounds such as the anthracycline antibiotics, and genetic defects known to increase the risk of heart failure.

By "congestive heart failure" is meant impaired cardiac function that renders the heart unable to maintain the normal blood output at rest or with exercise, or to maintain a normal cardiac output in the setting of normal cardiac filling pressure. A left ventricular ejection fraction of about 40% or less is indicative of congestive heart failure (by way of comparison, an ejection fraction of about 60% percent is normal). Patients in congestive heart failure display well-known clinical symptoms and signs, such as tachypnea, pleural effusions, fatigue at rest or with exercise, contractile dysfunction, and edema.

Congestive heart failure is readily diagnosed by well known methods (see, e.g., "Consensus recommendations for the management of chronic heart failure." Am. J. Cardiol., 83(2A):1A-38-A, 1999).

Relative severity and disease progression are assessed using well known methods, such as physical examination, echocardiography, radionuclide imaging, invasive hemodynamic monitoring, magnetic resonance angiography, and exercise treadmill testing coupled with oxygen uptake studies.

By "ischemic heart disease" is meant any disorder resulting from an imbalance between the myocardial need for oxygen and the adequacy of the oxygen supply. Most cases of ischemic heart disease result from narrowing of the coronary arteries, as occurs in atherosclerosis or other vascular disorders.

By "myocardial infarction" is meant a process by which ischemic disease results in a region of the myocardium being replaced by scar tissue.

By "cardiotoxic" is meant a compound that decreases heart function by directing or indirectly impairing or killing cardiomyocytes.

By "hypertension" is meant blood pressure that is considered by a medical professional (e.g., a physician or a nurse) to be higher than normal and to carry an increased risk for developing congestive heart failure.

By "treating" is meant that administration of a neuregulin or neuregulin-like polypeptide slows or inhibits the progression of congestive heart failure during the treatment, relative to the disease progression that would occur in the absence of treatment, in a statistically significant manner. Well known indicia such as left ventricular ejection fraction, exercise performance, and other clinical tests, as well as survival rates and hospitalization rates may be used to assess disease progression. Whether or not a treatment slows or inhibits disease progression in a statistically significant manner may be determined by methods that are well known in the art (see, e.g., SOLVD Investigators, N. Engl. J. Med. 327:685-691, 1992 and Cohn et al., N. Engl. J Med. 339:1810-1816, 1998).

By "decreasing progression of myocardial thinning" is meant maintaining hypertrophy of ventricular cardiomyocytes such that the thickness of the ventricular wall is maintained or increased.

By "inhibits myocardial apoptosis" is meant that neuregulin treatment inhibits death of cardiomyocytes by at least 10%, more preferably by at least 15%, still more preferably by at least 25%, even more preferably by at least 50%, yet more preferably by at least 75%, and most preferably by at least 90%, compared to untreated cardiomyocytes.

Stroke

Stroke or cerebrovascular accident (CVA) is a term used to refer to the rapidly developing loss of brain functions due to a disturbance in the blood vessels supplying blood to the brain. A stroke occurs when the blood supply to part of the brain is suddenly interrupted or when a blood vessel in the brain bursts, spilling blood into the spaces surrounding brain cells. Brain cells die when they no longer receive oxygen and nutrients from the blood or there is sudden bleeding into or around the brain. The symptoms of a stroke include sudden numbness or weakness, especially on one side of the body; sudden confusion or trouble speaking or understanding speech; sudden trouble seeing in one or both eyes; sudden trouble with walking, dizziness, or loss of balance or coordination; or sudden severe headache with no known cause. There are two forms of stroke: ischemic, which is due to blockage of a blood vessel supplying the brain (e.g., caused by thrombosis or embolism); and hemorrhagic, which results from bleeding into or around the brain.

Index for Therapeutic Window

For each disease application described herein, a target therapeutic window for GGF2 serum plasma levels is established. In accordance with the experimental results presented herein, when GGF2 is administered to a mammal afflicted with a neurological disorder associated with demyelination, GGF2 must be administered in a dosing regimen to achieve and maintain a narrow target therapeutic window of plasma GGF2 concentrations. As taught herein, precise dosing of GGF2 is necessary in order to achieve serum plasma levels of GGF2 required for therapeutic efficacy with respect to inducing myelination in a subject in need thereof.

In an embodiment of the invention directed to a patient in need of remyelination a particular embodiment, the target serum plasma level of GGF2 is about 0.01 nM.

In another embodiment of the invention directed to a patient in need of remyelination, GGF2 is administered at an amount of about 500 ng/kg of patient body weight.

The compositions of the present invention may be used in the treatment of a condition in a patient that includes establishing a therapeutically effective concentration of GGF2 in the patient in need thereof. The compositions may be used for building up a level and or maintaining a therapeutically effective concentration of GGF2 in the patient. Where desirable, the compositions of the present invention may be formulated to avoid large peaks in initial release of GGF2. The compositions of the present invention when administered to a patient in need thereof provide for the treatment of the above-indicated diseases. Preferably, the compositions are administered so as to achieve a therapeutically effective blood plasma level of GGF2 that is maintained in the patient for a period of at least 6 hours, preferably at least 8 hours, and more preferably at least about 10-12.

EXAMPLES

Materials and Methods

Antibodies

For immunofluorescence analysis, monoclonal antibody (SM194) to myelin basic protein (MBP) (Sternberger monoclonals) was used at a 1:500 dilution. For Western blot analysis, polyclonal antibodies to active erbB2 (p-Neu/Tyr 1248), erbB2 and erbB3 were all obtained from Santa Cruz and used at a 1:1000 dilution. Monoclonal antibody to phosphorylated Akt and polyclonal antibody to phosphorylated MAPK were purchased from Cell Signaling and were used at dilutions of 1:1000 and 1:500, respectively. Polyclonal antibodies to Akt and MAPK (Promega) were used at dilutions of 1:1000 and 1:5000, respectively.

Type-II and Type-III Neuregulin-1

Recombinant human glial growth factor-II (rhGGF-II, Type-II Nrg1) was obtained from Acorda Therapeutics, Inc. Recombinant human sensory and motor neuron derived factor (rhSMDF, Type-III Nrg1) was purchased from R&D Systems. In the present study, rhGGF-II and rhSMDF are referred simply as GGF (or GGF2) and SMDF, respectively. The GGF was the N-terminus 419 amino acid residues containing the EGF domain and the Ig-like domain. Accordingly, GGF is a soluble protein lacking a transmembrane and cytoplasmic domains.

Primary Rat Schwann Cell Culture

Schwann cells were prepared from sciatic nerves of newborn rats (1-2 day old) as described previously (Brockes et al., Brain Res. 1979; 165:105-118). For routine culture, Schwann cells were grown in Dulbecco's modified Eagle's medium (DMEM) with 10% fetal bovine serum (FBS) supplemented with EGF-domain neuregulin-1 (R&D Systems) (10 ng/ml) and Forskolin (2 μM). Cells between passage 2-4 were used in all experiments described in the text.

Dorsal Root Ganglion (DRG) Neuron-Schwann Cell Co-Culture

Dissociated DRG were prepared from embryonic day 14.5 rat embryos as described previously (Eldridge et al., J Cell Biol. 1987; 105(2):1023-34) and plated onto collagen (type-1 rat tail collagen)-coated 12 mm glass coverslips at a density of 1.25 DRG/coverslip. Five to six hours later, the cultures were flooded with neurobasal medium (Cellgro) supplemented with B27 (GIBCO), 20% glucose, NGF (50 ng/ml) and 5-fluorodeoxyuridine (FUdR, 10 μM) and maintained in the medium for additional 2-3 days in order to remove proliferating non-neuronal cells. Cultures were then switched to fresh medium without FUdR and maintained until the DRG axons reached the periphery of the coverslips. After the axonal networks were established, Schwann cells were plated onto the neurons at a density of 100,000 cells/coverslip. Four to five days later, cultures were switched to myelinating medium: Minimal Essential Medium (MEM) supplemented with 10% heat-inactivated FBS, 20% glucose, NGF (50 ng/ml) and ascorbic acid (50 μg/ml). Ten to eleven days later, myelination was assessed by immunostaining for MBP.

Superior Cervical Ganglion (SCG) Neuron-Schwann Cell Co-Culture

Dissociated SCG were prepared from postnatal day 1-2 rats as described previously and plated onto collagen-coated 12 mm glass coverslips at a density of 0.8 SCG/coverslip. Next day, the cultures were flooded with neurobasal medium supplemented with B27 (GIBCO), 20% glucose, NGF (50 ng/ml) and 5-fluorodeoxyuridine (FUdR, 10 μM) and maintained in the medium for an additional 2-3 days in order to remove proliferating non-neuronal cells. The cultures were switched back to fresh medium without FudR and maintained until the axons extended out to the periphery of the coverslips. Schwann cells were plated onto the neurons and maintained in neurobasal medium with supplements until the Schwann cells populate the axons (about 7-10 days). Myelination was initiated by placing the cultures in myelinating medium as described for DRG-Schwann cell co-culture. Forty days later, myelination was assessed by MBP immunostaining.

Immunoprecipitation and Western Blot Analysis

To prepare cell lysates, 90-95% confluent rat Schwann cells on 60 mm plates or co-cultures were washed twice in phosphate-buffered saline (PBS) and then lysed in 300 μl ice-cold lysis buffer (50 mM Tris HCl pH7.4, 1% NP-40, 0.25% Sodium Deoxycholate, 150 mM NaCl, 1 mM EGTA, 10 μg/ml Leupeptin, 2 μg/ml Aprotinin, 1 mM PMSF and 0.5 mM sodium orthovanadate). Lysates were cleared by centrifugation for 15 min at 14,000 rpm in the cold and the protein concentration of the supernatants was determined according to manufacturer specifications (Bio-Rad: Hercules, Calif.). For Western blot analysis, 50-70 μg of Schwann cell lysates were size-fractionated on 10% SDS-polyacrylamide gels and transferred onto PVDF membranes. After blocking in 5% milk, the membranes were incubated with appropriate primary antibodies prepared in blocking solution. After incubating with horseradish peroxidase conjugated secondary antibodies, the protein bands were visualized by enhanced chemiluminescence. For immunoprecipitation, 500 μg of Schwann cell lysates were incubated with 0.6 μg of primary antibody for 3 hours at 4° C., then incubated with 50 μl Sepharose A beads for 1 hour. Beads were washed 5 times in the lysis buffer and proteins bound to beads were fractionated on SDS-polyacrylamide gels and subjected to Western blot analysis.

Immunofluorescence Staining for MBP

DRG-Schwann cell or SCG-Schwann cell cultures were rinsed in phosphate buffered saline (PBS) then fixed in 4% paraformaldehyde for 20 minutes. After washing with PBS, samples were permeabilized in ice-cold methanol for 25 minutes then incubated in blocking solution (5% normal goat-serum+0.3% Triton X) for 1 hour at room temperature. This was followed by incubation with primary antibody prepared in blocking solution overnight. After washing with PBS, samples were incubated with Alexa-488 conjugated goat-anti-mouse secondary antibody for 45 minutes. Nuclei of cells were visualized by staining with DAPI.

Real-Time Quantitative PCR

Statistical Analysis

One way ANOVA was performed using SAS programming software with 95% significance level.

Results

The Inhibitory Function of GGF2 on Myelination is Mediated by the MAPK Activation An earlier study has shown that Nrg1 type II (GGF2), when added to Schwann cell-neuron co-cultures, inhibits myelination. It has also been reported that activation of Ras/Raf/MAPK pathway inhibits myelin-associated gene expression in Schwann cells, whereas activation of the PI3-kinase pathway promotes myelination, leading to a notion that the myelination state of Schwann cell is determined by the balance between PI3-kinase and Ras/Raf/MAPK pathways (Ogata et al. J Neurosci 2004; 24:6724-32). The present inventors predicted that if GGF2 acts via MAPK activation to inhibit myelination, inhibition of GGF2-induced MAPK activation would reverse the inhibitory effect on myelination. To assess the possibility that the inhibitory effect of GGF2 on myelination could be due to its ability to induce a robust MAPK activation in Schwann cells, the present inventors used a well-established in vitro myelinating culture system in which Schwann cells are co-cultured with dorsal root ganglion (DRG) neurons and induced to myelinate the associated axons by addition of ascorbic acid to the culture media. First, to determine the effect of GGF2 on MAPK activation in the co-cultures, primary Schwann cells were plated onto DRG neurons and allowed to propagate the axons. Once the cultures stopped proliferating, the co-cultures were stimulated with GGF2 at 0.6 nM. Twenty minutes later, cell lysates were prepared and MAPK activation was determined by Western blot analysis. In control co-cultures, there was a low level of active MAPK. As shown in FIG. 1, treatment with GGF2 further increased the level of MAPK activation. To determine whether the GGF2-induced MAPK activation could be blocked by treatment with U0126, a pharmacologic inhibitor of MAPK kinase, co-cultures were pre-treated with increasing concentrations (0.5, 1, 3 and 10 μM) of U0126 for 30 minutes prior to GGF2 stimulation and these concentrations were maintained in the culture medium. Control cultures were treated with the inhibitor in the absence of GGF2 treatment. In both control and experimental cultures, U0126-mediated MAPK inhibition was concentration-dependent, as indicated by the progressive decrease in the levels of phospho-MAPK. In cultures treated with GGF2 and U0126 at a concentration of 1 μM, the level of activation was reduced to the basal level, while at 10 μM U0126, MAPK activation in the co-culture was completely abolished. The U0126 had no effect on GGF2-induced PI3kinase activation.

In order to evaluate the effect of MAPK inhibition on myelination, co-cultures were treated with GGF2 in the presence or the absence of U0126 at the time of initiating myelination and the same conditions were maintained under the described myelinating condition. Control cultures were left untreated under the described myelinating condition. Ten to eleven days later, cultures were fixed and immunostained for myelin basic protein (MBP) to visualize myelin segments. In cultures treated with GGF2, there was a marked decrease in the number of myelin segments as shown previously, revealing the inhibitory effect of GGF2 on myelination. In cultures co-treated with U0126, however, there was a dose-dependent increase in myelination, indicating that blocking MAPK activation reversed the inhibitory effect of GGF2.

Figure 2:
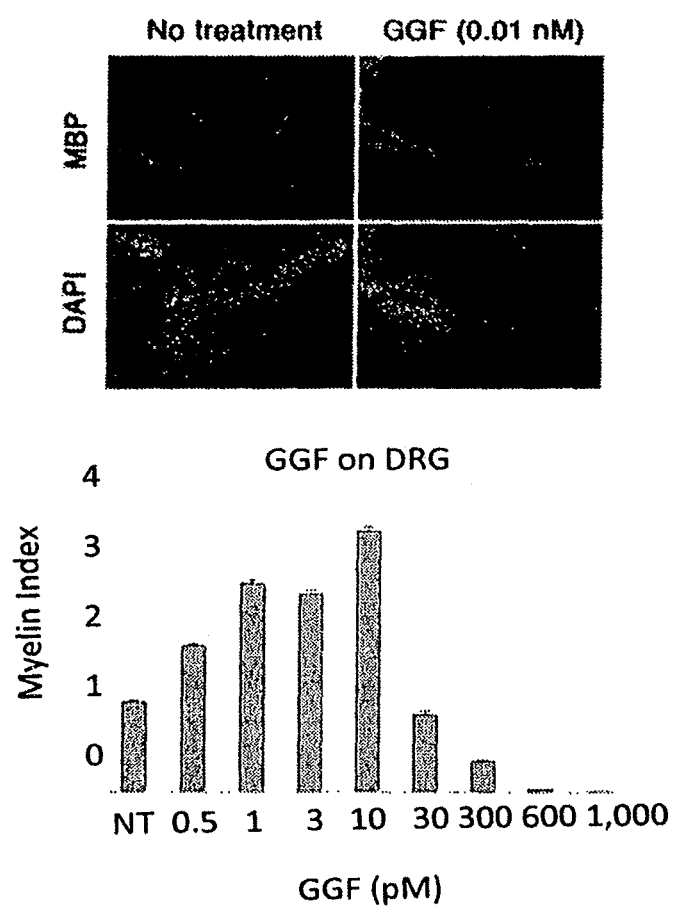
FIG. 2 shows GGF2 promotes myelination at low concentrations. Co-cultures were treated with GGF2 at concentrations ranging from 0.5 to 1000 pM (0.0005 to 1 nM) under myelinating conditions. Ten to twelve days later, myelination was assessed by MBP immunostaining. More particularly, the GGF2 concentrations from left to right are as follows: NT, 0.5 pM, 1 pM, 3 pM, 10 pM, 30 pM, 300 pM, 600 pM, and 1,000 pM, respectively. Ten to twelve days later, myelination was assessed by MBP immunostaining.

GGF2 Promotes Myelination at Low Concentrations:

Although the level of MAPK activation steadily increased in Schwann cells treated with increasing concentrations of GGF2, the present inventors observed that at low concentrations below 0.01 µM, while the level of Akt activation increased significantly above the basal level, there was no detectable level of MAPK activation. If the myelination state of a Schwann cell is determined by the balance between the Akt and MAPK activation, the present inventors sought to evaluate if the increase in Akt activation in the absence of MAPK activity at these concentrations is correlated with a positive effect on myelination. To investigate this potentiality, co-cultures were treated with GGF2 at concentrations ranging from 0.0005 and 0.03 nM at the time of initiating myelination. Cultures were later fixed and immunostained for MBP. As predicted based on the instant findings, there was an increase in the level of myelination in cultures treated with low doses of GGF2, ranging from 0.0005 to 0.01 nM, compared to the untreated control cultures. When quantitated, the result demonstrated that there was a dose-dependent increase in the number of myelin segments (FIG. 2): a 1.9-, 2.7-, and 3.5-fold increase in myelination relative to the control level, at 0.0005, 0.001 and 0.01 nM GGF2, respectively. At 0.03 nM, there was a drastic decrease in the level of myelination to a level close to, or slightly below the control cultures. Subsequent increases in the amount of GGF2 resulted in further decreases in myelination. Myelination responsive to GGF2 was completely inhibited at 0.6 nM GGF2. This concentration corresponded to the appearance of active MAPK in the co-cultures as shown in FIG. 1. These results suggest that GGF2 plays dual roles during myelination: one that promotes and the other that inhibits myelination, and the two opposing functions are determined by the dosage of GGF2 presented to the Schwann cells.

Figure 3:
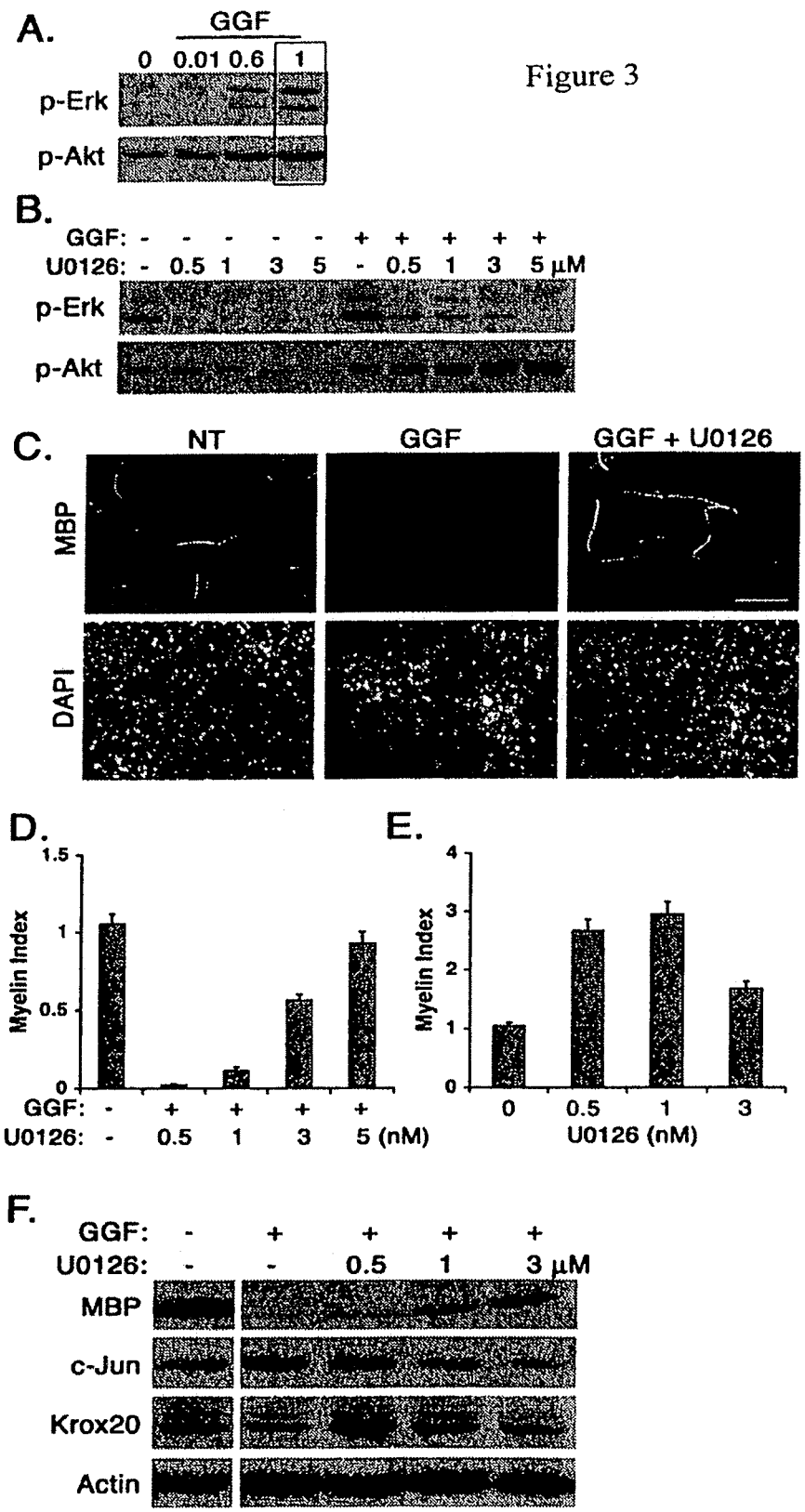
FIG. 3A-F show that an inhibitory effect of GGF on myelination is mediated by the Mek1/Erk activation. (A) Schwann cell DRG co-cultures were treated with GGF (0.01, 0.6, and 1 nM) and 45 minutes later the cell lysates were prepared and levels of active Erk (p-Erk) and Akt (p-Akt) were determined by Western blot analysis. At 1 nM (boxed), GGF induced activation of both Erk and Akt. (B) Inhibition of GGF-induced Erk activation in co-cultures. Schwann cell-DRG co-cultures were pre-treated with U0126 for 30 minutes then GGF (0.6 nM) was added in the continuous presence of U0126. After 45 minutes the cell lysates were prepared and level of p-Erk and p-Akt were determined. Treatment with U0126 inhibited both endogenous and GGF-induced Erk activation without affecting Akt activation. (C) Images of MBP+ myelin segments formed in co-cultures treated with GGF or GGF+U0126 (1 nM). Treatment with U0126 abolished the inhibitory effect of GGF and induced myelination. Control cultures were maintained without any treatment (NT). Scale bar: 100 μm. Quantification of the result is shown in (D). (E) Inhibition of endogenous Erk activity in co-cultures promotes myelination. Co-cultures were treated with increasing concentration of U0126 (0.5, 1 and 3 nM) under myelinating condition and 11 days later, myelination was analyzed as above. A significant increase in myelination was observed in cultures treated with U0126. Error bars indicate ±SE ($p<0.001$). (F) Inhibition of GGF-induced Erk activation is accompanied by a decrease in c-Jun and an increase in Krox20 expression. Co-cultures were maintained under myelinating condition in the presence of GGF or GGF+ U0126 (0.5, 1 and 3 nM) for 11 days and the cell lysates were analyzed for MBP, c-Jun and Krox 20 expression. Actin level served as a loading control. GGF-induced c-Jun expression was down-regulating with the treatment with U0126. Level of Krox 20 protein appeared increased in cultures treated with U0126.

The opposing functions of GGF2 are mediated by Mek/Erk activation: To investigate further the opposing functions of GGF2, additional experiments were performed. Previous studies have implicated Ras/Raf/Erk and PI-3 kinase, respectively, as negative and positive regulators of myelination, suggesting that a balance between the two is correlated with the myelination state of the Schwann cells. To delineate further the activation states of the pathways induced by GGF2, co-cultures were treated with the soluble GGF2 protein at 1 nM. The present inventors determined that at this concentration, GGF2 effectively inhibited myelination. Cell lysates were prepared 30 minutes following the GGF2 treatment and the presence of the phosphorylated proteins was determined by Western blot analysis (FIG. 3A). At 1 nM (FIG. 3A, boxed lanes) GGF2 increased Akt activation above the basal level. An increase in Erk activation was also observed in GGF2-treated cultures at this concentration. Concentrations of GGF2 as low as 0.6 nM were shown to be sufficient for Erk activation in GGF2 treated cultures.

To corroborate the above results and investigate further the correlative link between Erk activation and the inhibitory effect of GGF on myelination, additional experiments were performed. Accordingly, co-cultures were treated with GGF2 along with increasing concentrations of U0126, the above-described specific inhibitor of Mek1/Erk pathway. Western blot analysis presented in FIG. 3B shows that U0126 inhibited GGF2-induced Erk activation in a dosage-dependent manner while it had no effect on Akt activation. The low level of endogenous Erk activity normally observed in the co-culture system was also decreased with the drug treatment.

The present inventors further assessed the effect of Mek1/Erk inhibition on myelination. As shown in FIGS. 3C and 3D, addition of GGF2 at high concentration almost completely inhibited myelination in the co-cultures. In cultures co-treated U0126, however, the inhibitory effect of GGF2 was reversed, as indicated by the dosage-dependent increase in the level of myelination (FIGS. 3C and 3D). This result provides direct evidence that the inhibitory effect of GGF2 on myelination is mediated by the Erk activation. Interestingly, U0126 treatment in co-cultures in the absence of GGF2 also resulted in an increase in the level of myelination (FIG. 3E), which indicates that the endogenous Mek1/Erk activity functions as an intrinsic negative regulator of myelination.

Western blot analysis on lysates prepared from the co-cultures also revealed that GGF2 treatment increased expression of c-Jun protein, a negative regulator of Schwann cell differentiation and myelination. Subsequent inhibition of the GGF2-induced Mek1/Erk activity down-regulated c-Jun levels, which, in turn, was accompanied by an increase in myelin protein expression. Unlike the effect on c-Jun, U0126 treatment resulted in an increase in Krox20 expression in the co-cultures. This is in agreement with a recent report suggesting a cross antagonistic relationship between c-Jun and Krox20 in regulating myelination (Parkinson et al, 2008, Journal of Cell Biology 181:625-637).

Figure 4:
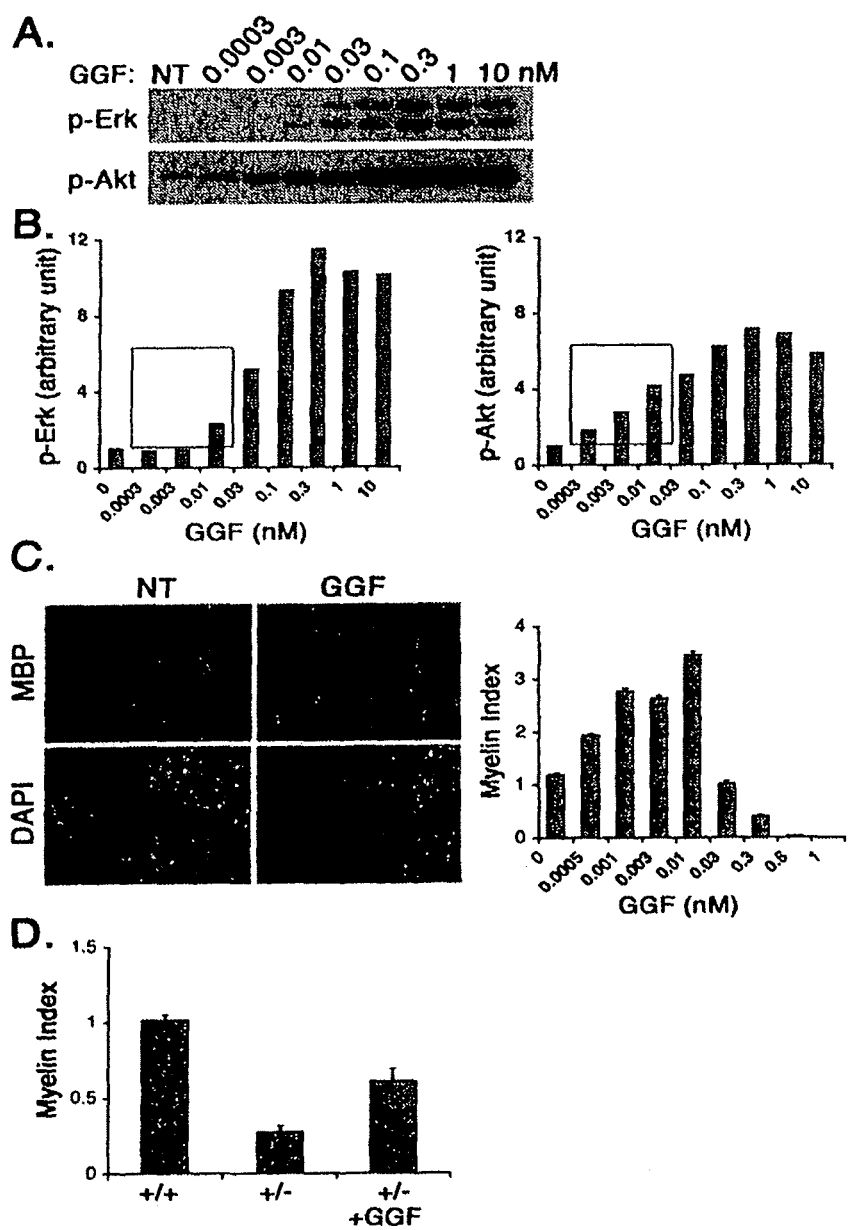
FIG. 4A-C shows that GGF promotes myelination at low concentration. (A) Schwann cells were treated with varying concentrations of GGF ranging from 0.0003 to 10 nM and 20 minutes later the cell lysates were prepared and the levels of Erk and Akt activation were analyzed by Western blot (top) and densitometric analysis (bottom). An increase in Akt activation appeared at lower concentration range (boxed) compared to Erk activation. (B) Co-cultures were treated with different concentrations of GGF (0.0005, 0.001, 0.003, 0.01, 0.03, 0.3, 0.6, and 1 nM) for 11 days under myelinating condition then fixed and immunostained for MBP and DAPI. Images of the control and cultures treated with 0.01 nM of GGF are shown along with the quantification of the result (right). A clear biphasic effect of GGF is shown that promotes myelination at low concentrations (0.0005 to 0.01 nM) while inhibiting the process at higher (0.3 nM and above) concentration. (C) Low concentration of GGF (0.01 nM) significantly increased myelination on CRD-Nrg1$^{+/-}$ neurons ($p=0.003$). Error bars show ±SEM. Data were analyzed by one-way ANOVA (*: $p<0.001$)

GGF2 promotes Schwann cell myelination: To corroborate and extend results presented herein and evaluate further the opposing functions of GGF2, the present inventors assessed the concentration-dependent effect of GGF2 on Ras/Raf/Erk and PI3-kinase activation in Schwann cells. Cells were treated with various concentrations of GGF2 ranging from 0.0003 to 10 nM and the level of Erk and Akt activation was determined by Western blot analysis. Images and the relative increase in the activation levels are presented in FIGS. 4A and 4B. The level of active Akt increased steadily beginning at the lowest dose tested, whereas Erk activation required higher concentrations of GGF2. The differential activation of the two pathways at low concentrations, as a result, generated a narrow window of doses (0.003 to 0.01 nM, boxed in FIG. 4B) in which Akt was the predominant pathway activated in response to GGF2. Next, the effect of various doses of GGF2 on myelination was determined in the co-culture system. At the low concentration window, GGF2 elicited a dosage-dependent promyelinating effect: 1.5-, 2.3-, 2.2- and 2.8-fold increase in myelination compared to the control cultures at 0.0005, 0.001, 0.003 and 0.01 nM of GGF2, respectively (FIG. 4C). As the concentration increased further, GGF2 began to inhibit myelination, coinciding with the appearance of Erk activation. The promyelinating effect of GGF2 was also demonstrated in CRD-Nrg1$^{+/-}$ co-cultures in which low doses of GGF2 rescued the myelination defect on the mutant axons (FIG. 4D).

Soluble Nrg1 can both promote and inhibit myelination: binary choice determined by the concentration: In the peripheral nervous system (PNS), GGF2 has been regarded as an Nrg1 isoform associated with the Schwann cell injury response. Ectopic in vivo expression of GGF-β3 in myelinating Schwann cells stimulates cell proliferation and induces demyelination (Huijbregts et al. J Neurosci 2003; 23:7269-80). Moreover, addition of high concentrations of GGF2 (e.g., those exceeding 0.25 nM GGF2) to Schwann cell-DRG neuron co-cultures has been shown to inhibit myelination (Zanazzi et al. J Cell Biol 2001; 152:1289-99). Thus, an unexpected result of the present study was the discovery that at low concentration, GGF2 exhibits myelination promoting effects. The promyelinating effect was, however, limited to a low concentration range and an increase in GGF2 concentration from this range results in inhibition of myelination as described previously. This is an intriguing finding as it demonstrates that soluble GGF2 can elicit two contrasting biological functions under the same cellular context solely based on the amount presented to the cell. It also suggests that threshold levels of GGF2 determine the promyelinating and inhibitory function during myelination. As demonstrated for the first time in the present study, this can be explained by concentration-dependent differential activation of the receptor downstream signaling effectors. More specifically, the present data show that the promyelinating function of GGF2 is observed at concentrations that preferentially activate Akt, while the transition into the inhibitory role at higher concentrations coincides with the appearance of Erk activation despite the continuous increase in the level active Akt. This result also supports the previous notion that the balance between PI3-kinase and Ras/Raf/Erk activation is crucial in determining the state of myelination in Schwann cells (Ogata et al. J Neurosci 2004; 24:6724-32). The present findings, however, provide direct evidence that activation of the Ras/Raf/Erk pathway functions as a negative regulator of myelination.

The inhibitory function Nrg1 on myelination is mediated through Erk/Mek1 activation: The inhibitory role of Ras/Raf/Erk pathway on myelination has been suggested previously by studies wherein expression of constitutively active Mek1 in Schwann cells blocks forskolin-induced myelin gene expression, whereas dominant-negative Ras blocks myelin gene down-regulation induced by Nrg1. Its direct effect on myelination, however, has not been elucidated prior to the instant results. As demonstrated herein, GGF2, when used above a threshold concentration, inhibits myelination in the co-cultures. The present inventors show herein that inhibition of Mek1/Erk1 activation restored myelination in GGF2-treated co-cultures, demonstrating that the inhibitory role of GGF2 was mediated through its Ras/Raf/Erk1 activation. The mechanism by which Mek1/Erk activation inhibits myelination is unclear. A possible mechanism includes suppression of myelin gene expression as described previously. Supportive of this suggestion, the present data revealed that an increase in myelination in U0126 treated cultures was accompanied by an increase in P0 expression. It is also possible that the Mek1/Erk pathway might modulate expression of transcription factors involved in myelination or Schwann cell differentiation. Recently it has been shown that ectopic expression of c-Jun in Schwann cells inhibits myelination, thus suggesting that c-Jun functions as a negative regulator of the myelin program. The present findings are consistent with this conclusion since the present inventors determined that GGF2 treatment that inhibits myelination is accompanied by c-Jun induction and furthermore, inhibition of the Nrg1-induced Mek1/Erk1 activity blocks c-Jun expression. This result suggests that the inhibitory function of Mek1/Erk1 on myelination is in part mediated through induction of c-Jun.

Another interesting finding of the present study is the presence of an intrinsic Mek1/Erk-dependent signal in the co-cultures that serves as a negative regulator of myelination. This was shown in an experiment in which treatment of normal myelinating co-cultures with U0126 promoted myelination. The nature of the signal that contributes to the Mek1/Erk1 activity during myelination is presently unknown, although it is likely to be axonal in origin, independent of the axonal CRD-Nrg1. Possible candidates are type I and II Ig-Nrg1 that are expressed by the PNS neurons and later released from the axonal membrane by proteolytic cleavage. Another possible Mek1/Erks activator is FGF-2, which is expressed in PNS neurons and the receptor for which is expressed on Schwann cells. Treatment with FGF-2 down-regulates myelin gene expression and inhibits myelination in vitro. Loss of FGF-2 expression results in an increase in the number of myelinated axons during sciatic nerve regeneration. Peripheral neurons also express PDGF and IGF, with the corresponding receptor tyrosine kinases expressed on the associated Schwann cells. It will be of a great interest to assess the regulatory role of these growth factors during myelination of the PNS.

Therapeutic use of GGF2: Experimental transplantation has provided overwhelming proof for the potential of repairing damaged nerves by transplantation of myelinating glial cells. Schwann cells are good candidates for such therapy as they are easily expanded in culture and offer the possibility of autologous transplantation to promote remyelination and restoration of nerve conduction at the demyelinated lesions not only in the PNS but also in the CNS. Remyelination by Schwann cells on adult regenerating axons, however, is often incomplete resulting in formation of thinner myelin sheath and shorter internode compared to normal nerves. Therefore, the present demonstration of the promyelinating function of GGF2 and the ability to avoid inadvertent hindrance of myelination due to GGF2 dose levels is significant as it provides a therapeutic strategy for the treatment of demyelinating diseases as well as for rebuilding myelin following nerve injury.

Other Embodiments

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure come within known or customary practice within the art to which the invention pertains and may be applied to the essential features hereinbefore set forth, and follows in the scope of the appended claims.

The invention claimed is:

1. A method of treating a patient afflicted with a disease or disorder associated with reduced levels of myelination, the method comprising administering a polypeptide comprising epidermal growth factor like (EGFL) domain of glial growth factor 2 (GGF2), and a Mek1/Erk pathway inhibitor, wherein the polypeptide is administered in an amount sufficient to elicit a plasma level of between about 0.0005 nM and about 0.01 nM of the polypeptide.

2. The method of claim 1, wherein the Mek1/Erk pathway inhibitor is selected from the group consisting of: (3R,4R)-4-[(3,4-dimethoxyphenyl)methyl]-3-[(4-hydroxy-3-methoxyphenyl)methyl]-2-tetrahydrofuranone, (2-(2'-amino-3'-methoxyphenyl)-oxanaphthalen-4-one]), 4-(4-Fluorophenyl)-2-(4-hydroxyphenyl)-5-(4-pyridyl)-1H-imidazole, 4-(4-fluorophenyl)-2-(4-methylsulfinylphenyl)-5-(4-pyridyl)-imidazole, anthra[1,9-cd]pyrazol-6(2H)-one, 1,4-diamino-2,3-dicyano-1,4-bis(2-aminophenylthio)butadiene, tipifarnib, sorafenib, TCCCGCCTGTGACATGCATT, 2-(2-Chloro-4-iodo-phenylamino)-N-cyclopropylmethoxy-3,4-difluoro-benzamide, and N-(2,3-dihydroxypropoxy)-3,4-difluoro-2-(2-fluoro-4-iodophenylamino)-benzamide.

3. The method of claim 1, wherein the disease or disorder associated with reduced levels of myelination is selected from the group consisting of: Guillain-Barre Syndrome, chronic inflammatory demyelinating polyneuropathy, peripheral demyelination due to traumatic injury, multiple sclerosis, optic neuritis, central demyelination due to traumatic injury, transverse myelitis, progressive multifocal leukoencephalopathy, Devic's disease (neuromyelitis optica), acute disseminated encephalomyelitis, adrenoleukodystrophy, and adrenoleukoneuropathy.

4. The method of claim 3, wherein the disease or disorder associated with reduced levels of myelination is multiple sclerosis.

5. The method of claim 3, wherein the disease or disorder associated with reduced levels of myelination is peripheral demyelination due to traumatic injury.

6. The method of claim 3, wherein the disease or disorder associated with reduced levels of myelination is central demyelination due to traumatic injury.

7. The method of claim 3, wherein the disease or disorder associated with reduced levels of myelination is optic neuritis.

8. The method of claim 1, wherein the amount administered is about 500 ng of the polypeptide per kg of body weight.

9. The method of method of claim 1, wherein the plasma level is about 0.01 nM of the polypeptide.

10. The method of claim 1, wherein the polypeptide is administered intravenously, intrathecally, or topically.

11. The method of method of claim 1, wherein the plasma level is about 0.0005 nM of the polypeptide.

12. The method of method of claim 1, wherein the plasma level is about 0.001 nM of the polypeptide.

13. The method of method of claim 1, wherein the plasma level is about 0.003 nM of the polypeptide.

* * * * *

SEQUENCE LISTING

<160> NUMBER OF SEQ ID NOS: 14

<210> SEQ ID NO 1
<211> LENGTH: 2003
<212> TYPE: DNA

<213> ORGANISM: Homo sapiens

<400> SEQUENCE: 1

| | | | | | |
|---|---|---|---|---|---|
| ggaattcctt | tttttttttt | tttttttctt | rrtttttttt | tgcccttata | cctcttcgcc | 60 |
| tttctgtggt | tccatccact | tcttcccct | cctcctccca | taaacaactc | tcctacccct | 120 |
| gcaccccaa | taaataaata | aaaggaggag | ggcaaggggg | gaggaggagg | agtggtgctg | 180 |
| cgaggggaag | gaaaagggag | gcagcgcgag | aagagccggg | cagagtccga | accgacagcc | 240 |
| agaagcccgc | acgcacctcg | caccatgaga | tggcgacgcg | cccccgcgccg | ctccgggcgt | 300 |
| cccggccccc | gggcccagcg | ccccggctcc | gccgcccgct | cgtcgccgcc | gctgccgctg | 360 |
| ctgccactac | tgctgctgct | ggggaccgcg | gccctggcgc | cggggcggc | ggccggcaac | 420 |
| gaggcggctc | ccgcggggc | ctcggtgtgc | tactcgtccc | cgcccagcgt | gggatcggtg | 480 |
| caggagctag | ctcagcgcgc | cgcggtggtc | atcgagggaa | aggtgcaccc | gcagcggcgg | 540 |
| cagcaggggg | cactcgacag | gaaggcggcg | gcggcggcgg | gcgaggcagg | ggcgtggggc | 600 |
| ggcgatcgcg | agccgccagc | cgcgggccca | cgggcgctgg | ggccgcccgc | cgaggagccg | 660 |
| ctgctcgccg | ccaacgggac | cgtgccctct | tggcccaccg | ccccggtgcc | cagcgccggc | 720 |
| gagcccgggg | aggaggcgcc | ctatctggtg | aaggtgcacc | aggtgtgggc | ggtgaaagcc | 780 |
| ggggggcttga | agaaggactc | gctgctcacc | gtgcgcctgg | ggacctgggg | ccaccccgcc | 840 |
| ttcccctcct | gcgggaggct | caaggaggac | agcaggtaca | tcttcttcat | ggagcccgac | 900 |
| gccaacagca | ccagccgcgc | gccggccgcc | ttccgagcct | ctttccccc | tctggagacg | 960 |
| ggccggaacc | tcaagaagga | ggtcagccgg | gtgctgtgca | agcggtgcgc | cttgcctccc | 1020 |
| caattgaaag | agatgaaaag | ccaggaatcg | gctgcaggtt | ccaaactagt | ccttcggtgt | 1080 |
| gaaaccagtt | ctgaatactc | ctctctcaga | ttcaagtggt | tcaagaatgg | gaatgaattg | 1140 |
| aatcgaaaaa | acaaaccaca | aaatatcaag | atacaaaaaa | agccagggaa | gtcagaactt | 1200 |
| cgcattaaca | aagcatcact | ggctgattct | ggagagtata | tgtgcaaagt | gatcagcaaa | 1260 |
| ttaggaaatg | acagtgcctc | tgccaatatc | accatcgtgg | aatcaaacgc | tacatctaca | 1320 |
| tccaccactg | ggacaagcca | tcttgtaaaa | tgtgcggaga | aggagaaaac | tttctgtgtg | 1380 |
| aatggagggg | agtgcttcat | ggtgaaagac | ctttcaaacc | cctcgagata | cttgtgcaag | 1440 |
| tgcccaaatg | agtttactgg | tgatcgctgc | caaaactacg | taatggccag | cttctacagt | 1500 |
| acgtccactc | cctttctgtc | tctgcctgaa | taggagcatg | ctcagttggt | gctgctttct | 1560 |
| tgttgctgca | tctcccctca | gattccacct | agagctagat | gtgtcttacc | agatctaata | 1620 |
| ttgactgcct | ctgcctgtcg | catgagaaca | ttaacaaaag | caattgtatt | acttcctctg | 1680 |
| ttcgcgacta | gttggctctg | agatactaat | aggtgtgtga | ggctccggat | gtttctggaa | 1740 |
| ttgatattga | atgatgtgat | acaaattgat | agtcaatatc | aagcagtgaa | atatgataat | 1800 |
| aaaggcattt | caaagtctca | cttttattga | taaaataaaa | atcattctac | tgaacagtcc | 1860 |
| atcttcttta | tacaatgacc | acatcctgaa | aagggtgttg | ctaagctgta | accgatatgc | 1920 |
| acttgaaatg | atggtaagtt | aattttgatt | cagaatgtgt | tatttgtcac | aaataaacat | 1980 |
| aataaaagga | aaaaaaaaa | aaa | | | | 2003 |

<210> SEQ ID NO 2
<211> LENGTH: 422
<212> TYPE: PRT
<213> ORGANISM: Homo sapiens

<400> SEQUENCE: 2

```
Met Arg Trp Arg Arg Ala Pro Arg Ser Gly Arg Gly Pro Arg
 1               5                  10                 15

Ala Gln Arg Pro Gly Ser Ala Ala Arg Ser Ser Pro Pro Leu Pro Leu
            20                  25                  30

Leu Pro Leu Leu Leu Leu Leu Gly Thr Ala Ala Leu Ala Pro Gly Ala
        35                  40                  45

Ala Ala Gly Asn Glu Ala Ala Pro Ala Gly Ala Ser Val Cys Tyr Ser
50                  55                  60

Ser Pro Pro Ser Val Gly Ser Val Gln Glu Leu Ala Gln Arg Ala Ala
65                  70                  75                  80

Val Val Ile Glu Gly Lys Val His Pro Gln Arg Gln Gln Gly Ala
                85                  90                  95

Leu Asp Arg Lys Ala Ala Ala Ala Gly Glu Ala Gly Ala Trp Gly
            100                 105                 110

Gly Asp Arg Glu Pro Pro Ala Ala Gly Pro Arg Ala Leu Gly Pro Pro
            115                 120                 125

Ala Glu Glu Pro Leu Leu Ala Ala Asn Gly Thr Val Pro Ser Trp Pro
130                 135                 140

Thr Ala Pro Val Pro Ser Ala Gly Glu Pro Gly Glu Glu Ala Pro Tyr
145                 150                 155                 160

Leu Val Lys Val His Gln Val Trp Ala Val Lys Ala Gly Gly Leu Lys
                165                 170                 175

Lys Asp Ser Leu Leu Thr Val Arg Leu Gly Thr Trp Gly His Pro Ala
            180                 185                 190

Phe Pro Ser Cys Gly Arg Leu Lys Glu Asp Ser Arg Tyr Ile Phe Phe
        195                 200                 205

Met Glu Pro Asp Ala Asn Ser Thr Ser Arg Ala Pro Ala Ala Phe Arg
210                 215                 220

Ala Ser Phe Pro Pro Leu Glu Thr Gly Arg Asn Leu Lys Lys Glu Val
225                 230                 235                 240

Ser Arg Val Leu Cys Lys Arg Cys Ala Leu Pro Pro Gln Leu Lys Glu
            245                 250                 255

Met Lys Ser Gln Glu Ser Ala Ala Gly Ser Lys Leu Val Leu Arg Cys
            260                 265                 270

Glu Thr Ser Ser Glu Tyr Ser Ser Leu Arg Phe Lys Trp Phe Lys Asn
            275                 280                 285

Gly Asn Glu Leu Asn Arg Lys Asn Lys Pro Gln Asn Ile Lys Ile Gln
290                 295                 300

Lys Lys Pro Gly Lys Ser Glu Leu Arg Ile Asn Lys Ala Ser Leu Ala
305                 310                 315                 320

Asp Ser Gly Glu Tyr Met Cys Lys Val Ile Ser Lys Leu Gly Asn Asp
            325                 330                 335

Ser Ala Ser Ala Asn Ile Thr Ile Val Glu Ser Asn Ala Thr Ser Thr
            340                 345                 350

Ser Thr Thr Gly Thr Ser His Leu Val Lys Cys Ala Glu Lys Glu Lys
            355                 360                 365

Thr Phe Cys Val Asn Gly Gly Glu Cys Phe Met Val Lys Asp Leu Ser
        370                 375                 380

Asn Pro Ser Arg Tyr Leu Cys Lys Cys Pro Asn Glu Phe Thr Gly Asp
385                 390                 395                 400

Arg Cys Gln Asn Tyr Val Met Ala Ser Phe Tyr Ser Thr Ser Thr Pro
            405                 410                 415
```

Phe Leu Ser Leu Pro Glu
            420

<210> SEQ ID NO 3
<211> LENGTH: 198
<212> TYPE: DNA
<213> ORGANISM: Homo sapiens

<400> SEQUENCE: 3
agccatcttg tcaagtgtgc agagaaggag aaaactttct gtgtgaatgg aggcgagtgc    60
ttcatggtga aagacctttc aaatccctca agatacttgt gcaagtgccc aaatgagttt   120
actggtgatc gctgccaaaa ctacgtaatg ccagcttct acagtacgtc cactcccttt    180
ctgtctctgc ctgaatag                                                  198

<210> SEQ ID NO 4
<211> LENGTH: 65
<212> TYPE: PRT
<213> ORGANISM: Homo sapiens

<400> SEQUENCE: 4

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Pro Asn Glu Phe Thr Gly Asp Arg Cys Gln Asn Tyr
        35                  40                  45

Val Met Ala Ser Phe Tyr Ser Thr Ser Thr Pro Phe Leu Ser Leu Pro
    50                  55                  60

Glu
65

<210> SEQ ID NO 5
<211> LENGTH: 192
<212> TYPE: DNA
<213> ORGANISM: Homo sapiens

<400> SEQUENCE: 5
agccatcttg tcaagtgtgc agagaaggag aaaactttct gtgtgaatgg aggcgagtgc    60
ttcatggtga aagacctttc aaatccctca agatacttgt gcaagtgcca acctggattc   120
actggagcga gatgtactga aatgtgcccc atgaaagtcc aaacccaaga aaaagcggag   180
gagctctact aa                                                        192

<210> SEQ ID NO 6
<211> LENGTH: 63
<212> TYPE: PRT
<213> ORGANISM: Homo sapiens

<400> SEQUENCE: 6

Ser His Leu Val Lys Cys Ala Glu Lys Glu Lys Thr Phe Cys Val Asn
1               5                   10                  15

Gly Gly Glu Cys Phe Met Val Lys Asp Leu Ser Asn Pro Ser Arg Tyr
            20                  25                  30

Leu Cys Lys Cys Gln Pro Gly Phe Thr Gly Ala Arg Cys Thr Glu Asn
        35                  40                  45

Val Pro Met Lys Val Gln Thr Gln Glu Lys Ala Glu Glu Leu Tyr
    50                  55                  60

```
<210> SEQ ID NO 7
<211> LENGTH: 183
<212> TYPE: DNA
<213> ORGANISM: Homo sapiens

<400> SEQUENCE: 7
agccatcttg tcaagtgtgc agagaaggag aaaactttct gtgtgaatgg aggcgagtgc      60
ttcatggtga aagacctttc aaatccctca agatacttgt gcaagtgccc aaatgagttt     120
actggtgatc gctgccaaaa ctacgtaatg gccagcttct acaaagcgga ggagctctac     180
taa                                                                   183

<210> SEQ ID NO 8
<211> LENGTH: 60
<212> TYPE: PRT
<213> ORGANISM: Homo sapiens

<400> SEQUENCE: 8

Ser His Leu Val Lys Cys Ala Glu Lys Glu Lys Thr Phe Cys Val Asn
 1               5                  10                  15

Gly Gly Glu Cys Phe Met Val Lys Asp Leu Ser Asn Pro Ser Arg Tyr
             20                  25                  30

Leu Cys Lys Cys Pro Asn Glu Phe Thr Gly Asp Arg Cys Gln Asn Tyr
         35                  40                  45

Val Met Ala Ser Phe Tyr Lys Ala Glu Glu Leu Tyr
     50                  55                  60

<210> SEQ ID NO 9
<211> LENGTH: 210
<212> TYPE: DNA
<213> ORGANISM: Homo sapiens

<400> SEQUENCE: 9
agccatcttg tcaagtgtgc agagaaggag aaaactttct gtgtgaatgg aggcgagtgc      60
ttcatggtga aagacctttc aaatccctca agatacttgt gcaagtgccc aaatgagttt     120
actggtgatc gctgccaaaa ctacgtaatg gccagcttct acaagcatct tgggattgaa     180
tttatggaga aagcggagga gctctactaa                                      210

<210> SEQ ID NO 10
<211> LENGTH: 69
<212> TYPE: PRT
<213> ORGANISM: Homo sapiens

<400> SEQUENCE: 10

Ser His Leu Val Lys Cys Ala Glu Lys Glu Lys Thr Phe Cys Val Asn
 1               5                  10                  15

Gly Gly Glu Cys Phe Met Val Lys Asp Leu Ser Asn Pro Ser Arg Tyr
             20                  25                  30

Leu Cys Lys Cys Pro Asn Glu Phe Thr Gly Asp Arg Cys Gln Asn Tyr
         35                  40                  45
```

Val Met Ala Ser Phe Tyr Lys His Leu Gly Ile Glu Phe Met Glu Lys
    50                  55                  60

Ala Glu Glu Leu Tyr
65

<210> SEQ ID NO 11
<211> LENGTH: 267
<212> TYPE: DNA
<213> ORGANISM: Homo sapiens

<400> SEQUENCE: 11
agccatcttg tcaagtgtgc agagaaggag aaaactttct gtgtgaatgg aggcgagtgc      60
ttcatggtga aagacctttc aaatccctca agatacttgt gcaagtgcca acctggattc    120
actggagcga gatgtactga gaatgtgccc atgaaagtcc aaacccaaga aaagtgccca    180
aatgagttta ctggtgatcg ctgccaaaac tacgtaatgg ccagcttcta cagtacgtcc    240
actccctttc tgtctctgcc tgaatag                                        267

<210> SEQ ID NO 12
<211> LENGTH: 88
<212> TYPE: PRT
<213> ORGANISM: Homo sapiens

<400> SEQUENCE: 12

Ser His Leu Val Lys Cys Ala Glu Lys Glu Lys Thr Phe Cys Val Asn
  1               5                  10                  15

Gly Gly Glu Cys Phe Met Val Lys Asp Leu Ser Asn Pro Ser Arg Tyr
             20                  25                  30

Leu Cys Lys Cys Gln Pro Gly Phe Thr Gly Ala Arg Cys Thr Glu Asn
         35                  40                  45

Val Pro Met Lys Val Gln Thr Gln Glu Lys Cys Pro Asn Glu Phe Thr
     50                  55                  60

Gly Asp Arg Cys Gln Asn Tyr Val Met Ala Ser Phe Tyr Ser Thr Ser
 65                  70                  75                  80

Thr Pro Phe Leu Ser Leu Pro Glu
                 85

<210> SEQ ID NO 13
<211> LENGTH: 252
<212> TYPE: DNA
<213> ORGANISM: Homo sapiens

<400> SEQUENCE: 13
agccatcttg tcaagtgtgc agagaaggag aaaactttct gtgtgaatgg aggcgagtgc      60
ttcatggtga aagacctttc aaatccctca agatacttgt gcaagtgcca acctggattc    120
actggagcga gatgtactga gaatgtgccc atgaaagtcc aaacccaaga aaagtgccca    180
aatgagttta ctggtgatcg ctgccaaaac tacgtaatgg ccagcttcta caaagcggag    240
gagctctact aa                                                        252

<210> SEQ ID NO 14
<211> LENGTH: 83
<212> TYPE: PRT
<213> ORGANISM: Homo sapiens

<400> SEQUENCE: 14

Ser His Leu Val Lys Cys Ala Glu Lys Glu Lys Thr Phe Cys Val Asn
  1               5                  10                  15

-continued

```
Gly Gly Glu Cys Phe Met Val Lys Asp Leu Ser Asn Pro Ser Arg Tyr
            20                  25              30

Leu Cys Lys Cys Gln Pro Gly Phe Thr Gly Ala Arg Cys Thr Glu Asn
        35              40                  45

Val Pro Met Lys Val Gln Thr Gln Glu Lys Cys Pro Asn Glu Phe Thr
        50              55              60

Gly Asp Arg Cys Gln Asn Tyr Val Met Ala Ser Phe Tyr Lys Ala Glu
65              70              75                      80

Glu Leu Tyr
```